Figure 2:
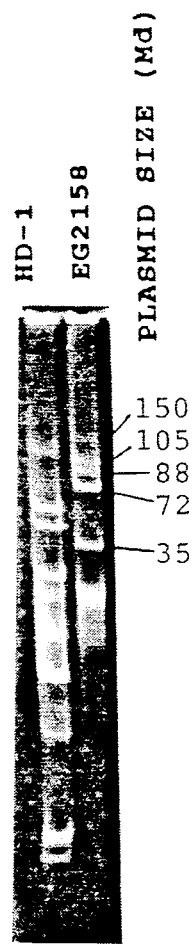

United States Patent [19]

Donovan et al.

[11] Patent Number: 5,024,837
[45] Date of Patent: Jun. 18, 1991

[54] COLEOPTERAN ACTIVE MICROORGANISMS, RELATED INSECTICIDE COMPOSITIONS AND METHODS FOR THEIR PRODUCTION AND USE

[76] Inventors: William P. Donovan, 650 Bayberry La., Yardley, Pa. 19067; Jose M. Gonzalez, Jr., 2211 Country La., West Trenton, N.J. 08628; Barry L. Levinson, 1 Millbrook La.; Anthony Macaluso, 2295 Princeton Pike, both of Lawrence, N.J. 08648

[21] Appl. No.: 47,945

[22] Filed: May 6, 1987

[51] Int. Cl.$^5$ .................. C12N 15/00; C12N 1/20; A61K 33/74
[52] U.S. Cl. .................. 424/93; 435/252.31; 435/122.5; 435/172.1; 435/320.1; 935/55; 935/56; 935/74
[58] Field of Search .............. 435/68, 70, 172.1, 172.3, 435/253, 832.834, 252.31, 320; 424/93

[56] References Cited

U.S. PATENT DOCUMENTS

| | | | |
|---|---|---|---|
| 4,016,265 | 4/1977 | Inoue et al. | 424/200 |
| 4,237,224 | 12/1980 | Cohen et al. | 435/68 |
| 4,467,036 | 8/1984 | Schepf et al. | 435/317 |
| 4,766,203 | 8/1988 | Krieg et al. | 530/370 |
| 4,771,131 | 9/1988 | Herrunstadt et al. | 536/27 |
| 4,797,279 | 1/1989 | Karamata et al. | 424/93 |

FOREIGN PATENT DOCUMENTS

| | | | |
|---|---|---|---|
| 221024 | 5/1987 | European Pat. Off. | 435/69.1 |
| 303379 | 2/1989 | European Pat. Off. | 435/69.1 |

OTHER PUBLICATIONS

Gonzalez et al., *Pnc Natl Acad Sci.* vol. 79, pp. 6951-6953, Nov. 1982, "Transfer of *Bacillus Triangular*" Puismodocoxy for X Endotutenjstmant of *B Triangrasis* and *Biceu*.
Gonzalez et al., *Plasmide* vol. 11, 1984, pp. 28-38 "A Large Transmissable Plasmide Reg for Crystal Protein Production in *Bacillus Trunjiersis Variety Israelewfor*".
Klier et al. *Mol. Gen. Geret.* vol. 191, Jul. 1983, pp. 257-262,"Mating Between *Bacillus Subtilus* and *Bacillus Triamjenio* and Transfer of Closed Crystal Genes".
Herrnstadt et al., *B. Utechrobyy* vol. 4, Apr. 1986, pp. 325-328, "A New Strain of *Bacillus Triungersis* with Activity Against Coleopteran Injects".
Donovan et al., Mol. Gen. Genet, (1988), 214:365-372.
McPherson et al., Bio/Technology (1988), 6:61-66.
Krieg et al., J. Appl. Ent. (1987) 104:417-424.
Herrnstadt et al., Gene (1987) 57:37-46.
Sekar et al., Proc. Natl. Acad. Sci. U.S.A. (1987) 84:7036-7040.
Höfte et al., Nucl. Acids Res. (1987), 15:7183.
Herrnstadt et al., Bio/Technology (1986) 4:305-308.
Aronson et al., Microbiol Rev. (1986) 50:1-24.
Bernhard, Fems Microbio. Lett. (1986) 33:261-265.
Chapman et al., "Conjugal Plasmid Transfer in Bacillus Thuringiensis" in Plasmids in Bacteria, Helinski et al., ed. Plenum Publish. Corp. (1985), pp. 453-467.
Carlton et al., "The Genetics and Molecular Biology of Bacillus Thuringiensis" in D. Dubnau, ed., The Molecular Biology of the Bacilli, vol. II, Academic Press. (1985) pp. 21-249.
Shibano et al., Gene (1985) 34:243-251.
Adang et al., Gene (1985) 36:289-300.
Waalwijk et al., Nucl. Acids Res. (1985) 13:8207-8217.
Sekar et al., Gene (1985) 33:151-158.

(List continued on next page.)

*Primary Examiner*—Robin L. Teskin

[57] ABSTRACT

This invention relates to *Bacillus thuringiensis* strains that have insecticidal activity against lepidopteran and coleopteran insects, the coleopteran-active endotoxin being produced by an acquired plasmid. This invention also relates to the crystalline protein toxin useful as a biological insecticide against Coleoptera which toxin is produced by the strain of *Bacillus thuringiensis*. This invention also relates to the expression in various microorganisms of the gene, known as *cryC*, which codes for this toxin, and for related novel insecticide compositions and methods for their use.

12 Claims, 13 Drawing Sheets

OTHER PUBLICATIONS

Gonzalez, Jr. et al., Plasmid (1984) 11:28–38.
Krieg et al., Anz. Schädlingskde. Pflangenschutz, Umweltschutz (1984) 57:145–148.
Ward et al., Febs Lett. (1984) 175:377–382.
Klier et al., Mol. Gen. Genet. (1983) 191:257–262.
Ward et al., Febs Lett. (1983) 158:45–49.
Krieg et al., Z. Angew. Ent. (1983) 96:500–508 (w/Translation).
Yamamoto et al., Arch. Biochem. Biophys. (1983) 227:223–241.
Wong et al., J. Biol. Chem. (1983) 258:1960–1967.
Gonzalez, Jr. et al., Proc. Natl. Acad. Sci. U.S.A. (1982) 79:6951–6955.
Gonzalez, Jr. et al., "Plasmid Transfer in Bacillus Thuringiensis", in Genetic Exchange Streips et al., ed. Marcel Dekker, Inc. (1982), pp. 85–95.
Yamamoto et al., Biochem. Biophys. Res. Commun. (1981) 103:414–421.
Roberts et al., Meth. Enzymol. (1979) 68:473–482.
Eckhardt, Plasmid (1978) 1:584–588.
Southern, J. Mol. Biol. (1975) 98:503–517.
Laemmli et al., J. Mol. Biol. (1973) 80:575–599.

FIGURE 1

STRAIN: EG2158

SOURCE: SOYBEAN GRAIN DUST, KANSAS

CRYSTAL PHENOTYPE: TWO CRYSTALS PER SPORANGIUM

1. RHOMBOID CRYSTAL (R-1)

2. FLAT DIAMOND-SHAPED CRYSTAL (F-1)

EG2158 TOXICITY: COLORADO POTATO BEETLE LARVAE.
NON-TOXIC TO LEPODOPTERAN LARVAE.

STANDARDS
EG 2158

NaBr sup
NaBr ppt

EG2158
NB032086-12B (-150,- F-1)
NB032086-12C (-35, n.c. )
EG2158 (REPURIF.)

NB032086-12B (C2)
" (M-27)
" (MedB)

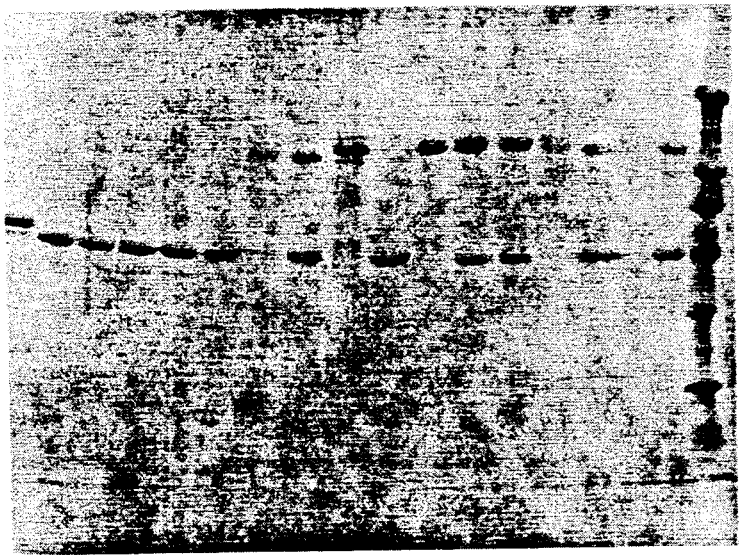
FIGURE 6(A)
FIGURE 6(B)

FIG. 8-1 cryC

```
          10        20        30        40        50        60
AAGCTTAATTAAAGATAATATCTTTGAATTGTAACGCCCCTCAAAAGTAAGAACTACAAA 70        80        90       100       110       120
AAAAGAATACGTTATATAGAAATATGTTTGAACCTTCTTCAGATTACAAATATATTCGGA 130       140       150       160       170       180
CGGACTCTACCTCAAATGCTTATCTAACTATAGAATGACATACAAGCACAACCTTGAAAA 190       200       210       220       230       240
TTTGAAAATATAACTACCAATGAACTTGTTCATGTGAATTATCGCTGTATTTAATTTTCT 250       260       270       280       290       300
CAATTCAATATATAATATGCCAATACATTGTTACAAGTAGAAATTAAGACACCCTTGATA 310       320       330       340       350       360
GCCTTACTATACCTAACATGATGTAGTATTAAATGAATATGTAAATATATTTATGATAAG 370       380       390       400       410       420
AAGCGACTTATTTATAATCATTACATATTTTTCTATTGGAATGATTAAGATTCCAATAGA 430       440       450       460       470       480
ATAGTGTATAAATTATTTATCTTGAAAGGAGGGATGCCTAAAAACGAAGAACATTAAAAA 490       500       510       520       530       540
CATATATTTGCACCGTCTAATGGATTTATGAAAAATCATTTTATCAGTTTGAAAATTATG 550       560       570       580       590       600
TATTATGATAAGAAAGGGAGGAAGAAAAATGAATCCGAACAATCGAAGTGAACATGATAC
                                 MetAsnProAsnAsnArgSerGluHisAspTh 610       620       630       640       650       660
AATAAAAACTACTGAAAATAATGAGGTGCCAACTAACCATGTTCAATATCCTTTAGCGGA
rIleLysThrThrGluAsnAsnGluValProThrAsnHisValGlnTyrProLeuAlaGl 670       680       690       700       710    PstI 720
AACTCCAAATCCAACACTAGAAGATTTAAATTATAAGAGTTTTTAAGAATGACTGCAGA
uThrProAsnProThrLeuGluAspLeuAsnTyrLysGluPheLeuArgMetThrAlaAs 730       740       750       760       770       780
TAATAATACGGAAGCACTAGATAGCTCTACAACAAAAGATGTCATTCAAAAAGGCATTTC
pAsnAsnThrGluAlaLeuAspSerSerThrThrLysAspValIleGlnLysGlyIleSe
       ──────▶
         790       800       810       820       830       840
CGTAGTAGGTGATCTCCTAGGCGTAGTAGGTTTCCCGTTTGGTGGAGCGCTTGTTTCGTT
rValValGlyAspLeuLeuGlyValValGlyPheProPheGlyGlyAlaLeuValSerPh 850       860       870       880       890       900
TTATACAAACTTTTTAAATACTATTTGGCCAAGTGAAGACCCGTGGAAGGCTTTTATGGA
eTyrThrAsnPheLeuAsnThrIleTrpProSerGluAspProTrpLysAlaPheMetGl
``` cryC

FIG. 8-2

```
         910       920       930       940       950       960
        ACAAGTAGAAGCATTGATGGATCAGAAAATAGCTGATTATGCAAAAAATAAAGCTCTTGC
        uGlnValGluAlaLeuMetAspGlnLysIleAlaAspTyrAlaLysAsnLysAlaLeuAl 970       980       990      1000      1010      1020
        AGAGTTACAGGGCCTTCAAAATAATGTCGAAGATTATGTGAGTGCATTGAGTTCATGGCA
        aGluLeuGlnGlyLeuGlnAsnAsnValGluAspTyrValSerAlaLeuSerSerTrpGl 1030      1040      1050      1060      1070      1080
        AAAAAATCCTGTGAGTTCACGAAATCCACATAGCCAGGGGCGGATAAGAGAGCTGTTTTC
        nLysAsnProValSerSerArgAsnProHisSerGlnGlyArgIleArgGluLeuPheSe 1090      1100      1110      1120      1130      1140
        TCAAGCAGAAAGTCATTTTCGTAATTCAATGCCTTCGTTTGCAATTTCTGGATACGAGGT
        rGlnAlaGluSerHisPheArgAsnSerMetProSerPheAlaIleSerGlyTyrGluVa 1150      1160      1170      1180      1190      1200
        TCTATTTCTAACAACATATGCACAAGCTGCCAACACACATTTATTTTTACTAAAAGACGC
        lLeuPheLeuThrThrTyrAlaGlnAlaAlaAsnThrHisLeuPheLeuLeuLysAspAl 1210      1220      1230      1240      1250      1260
        TCAAATTTATGGAGAAGAATGGGGATACGAAAAAGAAGATATTGCTGAATTTTATAAAAG
        aGlnIleTyrGlyGluGluTrpGlyTyrGluLysGluAspIleAlaGluPheTyrLysAr 1270      1280      1290      1300      1310      1320
        ACAACTAAAACTTACGCAAGAATATACTGACCATTGTGTCAAATGGTATAATGTTGGATT
        gGlnLeuLysLeuThrGlnGluTyrThrAspHisCysValLysTrpTyrAsnValGlyLe 1330      1340      1350      1360      1370      1380
        AGATAAATTAAGAGGTTCATCTTATGAATCTTGGGTAAACTTTAACCGTTATCGCAGAGA
        uAspLysLeuArgGlySerSerTyrGluSerTrpValAsnPheAsnArgTyrArgArgGl 1390      1400      1410      1420      1430      1440
        GATGACATTAACAGTATTAGATTTAATTGCACTATTTCCATTGTATGATGTTCGGCTATA
        uMetThrLeuThrValLeuAspLeuIleAlaLeuPheProLeuTyrAspValArgLeuTy 1450      1460      1470      1480      1490      1500
        CCCAAAAGAAGTTAAAACCGAATTAACAAGAGACGTTTTAACAGATCCAATTGTCGGAGT
        rProLysGluValLysThrGluLeuThrArgAspValLeuThrAspProIleValGlyVa 1510      1520      1530      1540      1550      1560
        CAACAACCTTAGGGGCTATGGAACAACCTTCTCTAATATAGAAAATTATATTCGAAAACC
        lAsnAsnLeuArgGlyTyrGlyThrThrPheSerAsnIleGluAsnTyrIleArgLysPr 1570      1580      1590      1600      1610      1620
        ACATCTATTTGACTATCTGCATAGAATTCAATTTCACACGCGGTTCCAACCAGGATATTA
        oHisLeuPheAspTyrLeuHisArgIleGlnPheHisThrArgPheGlnProGlyTyrTy 1630      1640      1650      1660      1670      1680
        TGGAAATGACTCTTTCAATTATTGGTCCGGTAATTATGTTTCAACTAGACCAAGCATAGG
        rGlyAsnAspSerPheAsnTyrTrpSerGlyAsnTyrValSerThrArgProSerIleGl 1690      1700      1710      1720      1730      1740
        ATCAAATGATATAATCACATCTCCATTCTATGGAAATAAATCCAGTGAACCTGTACAAAA
        ySerAsnAspIleIleThrSerProPheTyrGlyAsnLysSerSerGluProValGlnAs 1750      1760      1770      1780      1790      1800
        TTTAGAATTTAATGGAGAAAAAGTCTATAGAGCCGTAGCAAATACAAATCTTGCGGTCTG
        nLeuGluPheAsnGlyGluLysValTyrArgAlaValAlaAsnThrAsnLeuAlaValTr
``` cryC

FIG. 8-3

```
        1810       1820       1830       1840       1850       1860
      GCCGTCCGCTGTATATTCAGGTGTTACAAAAGTGGAATTTAGCCAATATAATGATCAAAC
      pProSerAlaValTyrSerGlyValThrLysValGluPheSerGlnTyrAsnAspGlnTh 1870       1880       1890       1900       1910       1920
      AGATGAAGCAAGTACACAAACGTACGACTCAAAAAGAAATGTTGGCGCGGTCAGCTGGGA
      rAspGluAlaSerThrGlnThrTyrAspSerLysArgAsnValGlyAlaValSerTrpAs 1930       1940       1950       1960       1970       1980
      TTCTATCGATCAATTGCCTCCAGAAACAACAGATGAACCTCTAGAAAAGGGATATAGCCA
      pSerIleAspGlnLeuProProGluThrThrAspGluProLeuGluLysGlyTyrSerHi 1990       2000       2010       2020       2030       2040
      TCAACTCAATTATGTAATGTGCTTTTTAATGCAGGGTAGTAGAGGAACAATCCCAGTGTT
      sGlnLeuAsnTyrValMetCysPheLeuMetGlnGlySerArgGlyThrIleProValLe 2050       2060       2070       2080       2090       2100
      AACTTGGACACATAAAAGTGTAGACTTTTTTAACATGATTGATTCGAAAAAAATTACACA
      uThrTrpThrHisLysSerValAspPhePheAsnMetIleAspSerLysLysIleThrGl 2110       2120       2130       2140       2150       2160
      ACTTCCGTTAGTAAAGGCATATAAGTTACAATCTGGTGCTTCCGTTGTCGCAGGTCCTAG
      nLeuProLeuValLysAlaTyrLysLeuGlnSerGlyAlaSerValValAlaGlyProAr 2170       2180       2190       2200       2210       2220
      GTTTACAGGAGGAGATATCATTCAATGCACAGAAAATGGAAGTGCGGCAACTATTTACGT
      gPheThrGlyGlyAspIleIleGlnCysThrGluAsnGlySerAlaAlaThrIleTyrVa 2230       2240       2250       2260       2270       2280
      TACACCGGATGTGTCGTACTCTCAAAAATATCGAGCTAGAATTCATTATGCTTCTACATC
      lThrProAspValSerTyrSerGlnLysTyrArgAlaArgIleHisTyrAlaSerThrSe 2290       2300       2310       2320       2330       2340
      TCAGATAACATTTACACTCAGTTTAGACGGGGCACCATTTAATCAATACTATTTCGATAA
      rGlnIleThrPheThrLeuSerLeuAspGlyAlaProPheAsnGlnTyrTyrPheAspLy 2350       2360       2370       2380       2390       2400
      AACGATAAATAAAGGAGACACATTAACGTATAATTCATTTAATTTAGCAAGTTTCAGCAC
      sThrIleAsnLysGlyAspThrLeuThrTyrAsnSerPheAsnLeuAlaSerPheSerTh 2410       2420       2430       2440       2450       2460
      ACCATTCGAATTATCAGGGAATAACTTACAAATAGGCGTCACAGGATTAAGTGCTGGAGA
      rProPheGluLeuSerGlyAsnAsnLeuGlnIleGlyValThrGlyLeuSerAlaGlyAs 2470       2480       2490       2500       2510       2520
      TAAAGTTTATATAGACAAAATTGAATTTATTCCAGTGAATTAAATTAACTAGAAAGTAAA
      pLysValTyrIleAspLysIleGluPheIleProValAsnEnd 2530       2540       2550       2560       2570       2580
      GAAGTAGTGACCATCTATGATAGTAAGCAAAGGATAAAAAAATGAGTTCATAAAATGAAT 2590       2600       2610       2620       2630       2640
      AACATAGTGTTCTTCAACTTTCGCTTTTTGAAGGTAGATGAAGAACACTATTTTTATTTT 2650       2660       2670       2680       2690       2700
      CAAAATGAAGGAAGTTTTAAATATGTAATCATTTAAAGGGAACAATGAAAGTAGGAAATA
```

FIG. 8-4 cryC

```
           2710      2720      2730      2740      2750      2760
AGTCATTATCTATAACAAAATAACATTTTTATATAGCCAGAAATGAATTATAATATTAAT 2770      2780      2790      2800      2810      2820
CTTTTCTAAATTGACGTTTTTCTAAACGTTCTATAGCTTCAAGACGCTTAGAATCATCAA 2830      2840      2850      2860      2870      2880
TATTTGTATACAGAGCTGTTGTTTCCATCGAGTTATGTCCCATTTGATTCGCTAATAGAA 2890      2900      2910      2920      2930      2940
CAAGATCTTTATTTTCGTTATAATGATTGGTTGCATAAGTATGGCGTAATTTATGAGGGC 2950      2960      2970      2980
TTTTCTTTTCATCAAAAGCCCTCGTGTATTTCTCTGTAAGCTT
```

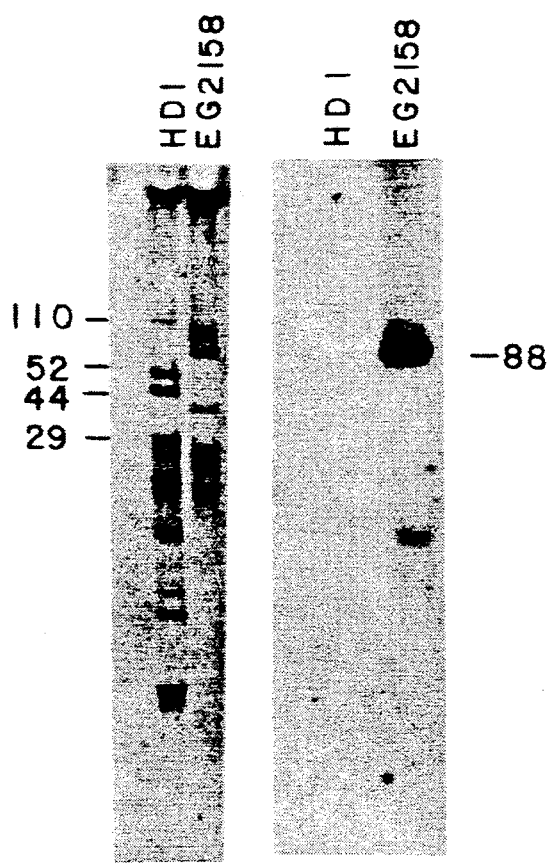

COLEOPTERAN ACTIVE MICROORGANISMS, RELATED INSECTICIDE COMPOSITIONS AND METHODS FOR THEIR PRODUCTION AND USE 1.0 Introduction
2.0 Background of the Invention
2.1 Commercial Pesticides: General Considerations
2.2. Biological Pesticides
2.3 *Bacillus thuringiensis* and Delta-Endotoxins
2.4 Coleopteran-Active *Bacillus thuringiensis*
2.5 Delta-Endotoxin Gene Cloning
3.0 Summary of the Invention
4.0 Brief Description of the Figures
5.0 Description of the Invention
5.1 Coleopteran Active *Bacillus thuringiensis*
5.2 Transconjugants Having Coleopteran and Lepidopteran Activity
5.3 Recombinant DNA Technology and Gene Expression
5.4 Cloning of the cryC Toxin Gene from *Bacillus thuringiensis* Strain EG2158
5.5 Oligonucleotide Probe for the cryC Gene
5.6 Construction of a Plasmid Library Enriched for the cryC Gene
5.7 Colony Hybridization and Isolation of a 2.6 kb HindIII Fragment Containing the cryC Gene
5.8 Location of the cryC Gene on the Cloned 2.6 kb HindIII Fragment
5.9 DNA Sequence of the Cloned cryC Gene
5.10 Use of the Cloned cryC Gene as a Specific Hybridization Probe
5.10.1 Identification of native B.t. Plasmids Containing cryC Genes
5.11 Transformation of the cryC Gene into Heterologous Microorganisms
5.12 Transformation of cryC Gene into Plants
5.13 Products and Formulations Incorporating the Coleopteran Active Toxin
6.0 Examples
6.1 Example 1—Transformation of the cryC Gene into *Bacillus megaterium*
6.2 Example 2—Bioassay of the Expression Product of the Cloned cryC Gene in *B. Megaterium*
7.0 Deposit of Microorganisms

1.0 INTRODUCTION

This relates to biologically pure cultures of *Bacillus thuringiensis* strains which have insecticidal activity at least against insects of the order Coleoptera. This invention also relates to the crystalline protein toxin which is useful as a biological insecticide against coleopteran insects. The toxin is naturally produced by this strain of *Bacillus thuringiensis*. This invention also relates to the expression in various microorganisms of the gene, herein referred to as cryC, which codes for the coleopteran active toxin and for related novel insecticide compositions incorporating the toxin itself and microorganisms transformed with the cryC gene.

2.0 BACKGROUND OF THE INVENTION

2.1 Commercial Pesticides: General Considerations

Each year, significant portions of the world's commercially important agricultural crops are lost to insects and other pest infestation. The damage wrought by these pests extends to all areas of commercially important plants including foods, textiles, and various domestic plants, and the economic damage runs well into the millions of dollars. Thus, protection of crops from such infestations is of paramount concern.

Broad spectrum pesticides are most commonly used for crop protection, but indiscriminate use of these agents can lead to disruption of the plant's natural defensive agents. Furthermore, because of their broad spectrum of activity, the chemical pesticides may destroy non-target organisms such as beneficial insects and parasites of destructive pests. These are also frequently toxic to animals and humans and, thus, pose environmental hazards when applied.

Additionally, insects and other organisms have frequently developed resistance to these pesticides when repeatedly exposed to them. In addition to reducing the utility of the pesticide, resistant strains of minor pests may become major infestation problems due to the reduction of beneficial parasitic organisms.

This is a major problem encountered in using broad spectrum pesticides. What is needed is a biodegradable pesticide that combines a narrower spectrum of activity with the ability to maintain its activity over an extended period of time, i.e., to which resistance develops much more slowly, or not at all. Biopesticides appear to be useful in this regard.

2.2. Biological Pesticides

Biopesticides, also called biorationals, make use of naturally occurring pathogens to control insects, fungal, and weed infestations of agricultural crops. Such substances may comprise a bacterium which produces a substance toxic to the infesting agent (such as a toxin), with or without a bacterial growth medium. Such bacteria, which can be applied directly to the plants by standard methods of application, are typically less harmful to non-target organisms, and to the environment as a whole, in comparison to chemical pesticides.

The use of biological methods of pest control was first suggested in 1895 when a fungal disease was discovered in silkworms. It was not until 1940, however, when spores of the milky disease bacterium *Bacillus popilliae* were used to control the Japanese beetle, that successful biological pest control was first achieved. The bacterium, named *Bacillus thuringiensis* (hereinafter referred to alternatively as "B.t."or "BT"), a bacteria that produces a toxin fatal to caterpillars and other insects, is currently the most widely used biopesticide. In the late 1960's, the discovery of HD-1, a highly toxic strain of B.t., set the stage for commercial use of iopesticides.

2.3 *Bacillus Thuringiensis* and Delta-Endotoxins

*Bacillus thuringiensis* is a widely distributed, rod shaped, aerobic, spore-forming microorganism. During its sporulation cycle B.t. forms proteins known as protoxins or delta-endotoxins. These protoxins are deposited in B.t. as parasporal, crystalline inclusions or as part of the spore coat. The pathogenicity of B.t. to a variety of sensitive insects, such as those in the orders Lepidoptera and Diptera, is essentially due to this parasporal crystal, which may represent over 20% of the dry weight of the B.t. cell at the time of sporulation.

The parasporal crystal is active in the insect only after ingestion. For instance, after ingestion by a lepidopteran insect, the alkaline pH and proteolytic enzymes in the mid-gut activate the crystal allowing the release of the toxic components. These toxic components poison the mid-gut cells causing the insect to cease feeding and, eventually, to die. In fact, B.t. has proven to be an effective and environmentally safe insecticide in dealing with lepidopteran pests.

It has been reported that different strains of B.t produce serologically different parasporal crystals. However, one of the predominant crystal forms produced by many of the B.t. strains is a form known as P-1. P-1 has a molecular weight of about 130,000-daltons and may also be present in the spore coat. The genes for the parasporal crystal P-1 and those of most of the other protein crystals, have been discovered to reside on any one of a large number of different plasmids of varying size in B.t.

2.4 Coleopteran-Active *Bacillus thuringiensis*

The first isolation of coleopteran-toxic B.t. was reported in 1983. (A. Krieg et al. (1983) *Z.ang.Ent.* 96, 500–508; Ibid. (1984) *Anz. Schaedlingskde, Pflanzenschutz, Umweltschutz* 57, 145–150) This strain makes a single crystal reported to be comprised of proteins of 68 and 50 kDa (K. Bernhard *FEMS Microbiol. Lett.* 33, 261–265 (1986). This strain was given the designation *Bacillus thuringiensis* var. *tenebrionis*. It was reported that larvae of Lepidoptera and Nematocera were not sensitive to spores and crystals of this strain. A similar strain reported by Mycogen Corp. (San Diego, Calif.), produces a 64 kDa protein. (C. Herrnstadt et al. Bio/Technology 4, 305–308 (1986)).

2.5 Delta-Endotoxin Gene Cloning

Since B.t. toxin genes typically reside on plasmids and their products have proven to be effective insecticides which are readily isolated when in crystalline form or when associated with spore formation, they have been the subject of a great deal of scientific study, particularly with regard to gene isolation and cloning procedures.

The gene which codes for P-1 has been isolated from B.t. subspecies *kurstaki* strain HD-1-Dipel, and cloned and expressed in *E. coli* [Schnepf et al., U.S. Pat. No. 4,467,036]. The protein product, P-1, was determined to be toxic to a lepidopteran insect (tobacco hornworm larvae). The nucleotide sequence of the promoter region and part of the coding region of the crystal protein gene for P-1 have also been determined [H. P. Wong et al., The Journal of Biological Chemistry, Vol 258, No. 3, pp.1960–1967 (1983)]. The entire nucleotide sequence of this gene has also been determined and the delta-endotoxin protein itself has been expressed in a transformed *E. coli* strain. [M. J. Adang et al., Gene, Vol, 36, pp. 289–300 (1985) and PCT application PCT/US85/01665, for: B.t. Crystal Protein Gene Toxin Segment, (1985)].

The genes for other delta-endotoxin forms have also been cloned and expressed in *E. coli*. Recombinant plasmids containing a mosquitocidal delta-endotoxin gene from B.t. var. *israelensis* was inserted into an *E. coli* vector. A 26,000-dalton polypeptide was synthesized by *E. coli* transformed with this vector. This polypeptide was shown to be lethal to insects in the order Diptera (mosquitos). [E. S. Ward et al., FEBS Vol. 175, 2, pp.377–382, 1984]. The nucleotide sequence of the gene Acids Research, Vol.13, No. 22, pp.8207–8217, (1985)]. Another B.t. var. israelensis gene encoding a 130 KDa crystal protein was cloned and used to transform *Bacillus megaterium* and *Bacillus subtilis*. Both *B. megaterium* and *B. subtilis* expressed crystalline inclusions during sporulation which inclusions were determined to be toxic to the larvae of *Aedes aegypti*. [V. Sekar et al., Gene, Vol. 33, pp. 151–158, (1985)].

Another delta-endotoxin protein crystal was derived from B.t. subspecies sotto. The gene coding for this crystalline protein was cloned in a vector and then expressed in a transformed *E. coli*. This gene codes for a 144,000 dalton peptide (934 amino acid residues). The nucleotide sequence for the gene and the amino acid sequence of the corresponding protein (as deduced from the DNA sequence) have been reported. [Y. Shibano et al., Gene, Vol. 34, pp.243–251, (1985)].

It has also been recognized that another major delta-endotoxin protein is produced by several subspecies of B.t. [T. Yamamoto, Biochem. and Biophys. Res. Comm. Vol. 103, No. 2, pp. 414–421 (1981); T. Yamamoto et al. Archives of Biochemistry and Biophysics, Vol. 227, No. 1, pp. 223–241 (1983)]. This delta-endotoxin has been identified as P-2 and isolated from B.t. var. *kurstaki* (HD-1). This delta-endotoxin has a molecular weight of approximately 65,000 and is known to be toxic to lepidopteran and dipteran insects. In contrast, P-1 is active only against insects of the order Lepidoptera.

To date, although the rare coleopteran active organisms have been isolated neither the toxin protein nor the gene coding for it have been purified or sequenced. This fact has rendered it impossible to provide a means for expressing this uniquely active delta-endotoxin protein in an organism other than B.t. The availability of a cloned gene coding for coleopteran-active protein toxin would enable the enhanced production of this protein in heterologous organisms free of other delta-endotoxins.

3.0 SUMMARY OF THE INVENTION

This invention relates to a biologically pure culture of a *Bacillus thuringiensis* strain which has insecticidal activity against insects of the order Coleoptera. This invention also relates to a coleopteran active delta-endotoxin produced by a strain of *Bacillus thuringiensis*, the DNA sequence for the gene which codes for this protein and novel insecticides incorporating this protein and/or organisms producing it. More specifically, this invention relates to the cloning and transformation of microorganisms with the cryC gene coding for the coleopteran active delta-endotoxin. In addition, this invention is useful in permitting the transformation of a non-sporulating microorganism with the gene coding for the coleopteran active toxin so that it may be produced during virtually all stages of microorganism growth and, thereby, not be limited to production only during a sporulation stage.

It is, therefore, an object of this invention to provide a biologically pure culture of a *Bacillus thuringiensis* strain which has insecticidal activity against insects of the order Coleoptera. It is an additional object of this invention to provide a homogeneous coleopteran active protein produced by the isolated gene referred to herein as cryC. This protein may be produced by the process of transforming a microorganism, sporulating or non-sporulating, such as *Bacillus megaterium* or *E. coli* or a different strain of B.t. with the cloned cryC gene. This process, by virtue of selection of the appropriate host and vector, would permit high yield production of the delta-endotoxin such that it is possible to derive a substantially homogeneous preparation of it, i.e. minus any contamination by other varieties of delta-endotoxins. The coleopteran active protein and/or the transformed host may be utilized in a variety of insecticidal compositions.

It is further an object of this invention to provide an organism, other than the native B.t. host, transformed with the cryC gene. This foreign transformed host enables the production of the coleopteran active delta-endotoxin under more desirable and/or selective culturing conditions.

It is an additional object of this invention to provide strains of Bacillus thuringiensis which have a dual activity not found in nature, that is, an insecticidal activity against insects in the orders Lepidoptera and Coleoptera.

It is another object of this invention to provide a DNA probe useful for detecting the presence of the cryC gene in the various Bacillus thuringiensis strains. This DNA probe also enables the screening of various strains of B.t. for the possible presence of related genes coding for proteins sharing a common homology with the coleopteran active protein and the isolation of these related genes. It is a further object of this invention to provide a method for controlling insects of the order Coleoptera with coleopteran active Bacillus thuringiensis or organisms transformed with the cryC gene, which renders that strain active against Coleoptera.

It is also an object of this invention to provide a method for controlling insects in both the orders Lepidoptera and Coleoptera with transconjugant Bacillus thuringiensis strains which are active against both types of insects, strains which are unknown in the wild. All of the above embodiments of this invention will be described in greater detail in the description of the invention which follows.

4 0 BRIEF DESCRIPTION OF THE FIGURES

FIG. 1 shows a comparison of the crystal types produced by coleopteran-toxic Bacillus thuringiensis by strain EG 2158 and their appearance within the microorganism. In the drawings of the rhomboid crystal and flat diamond-shaped crystal, a top view of the respective crystals is shown on the left and a side view is shown on the right FIG. 2 is a photograph of a gel electrophoresis showing the respective plasmid arrays of HD-1 and EG2158.

Figure 3:
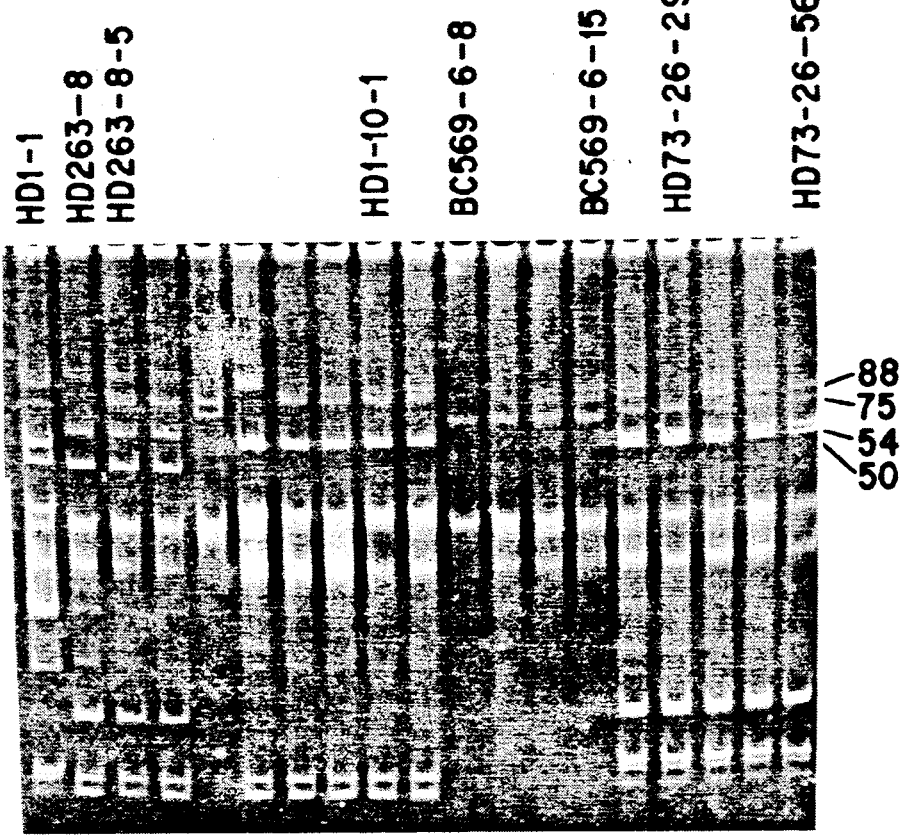

FIG. 3 is a photograph of a gel electrophoresis showing the respective plasmid arrays of transconjugants harboring coleopteran and lepidopteran active toxin plasmids.

Figure 4:
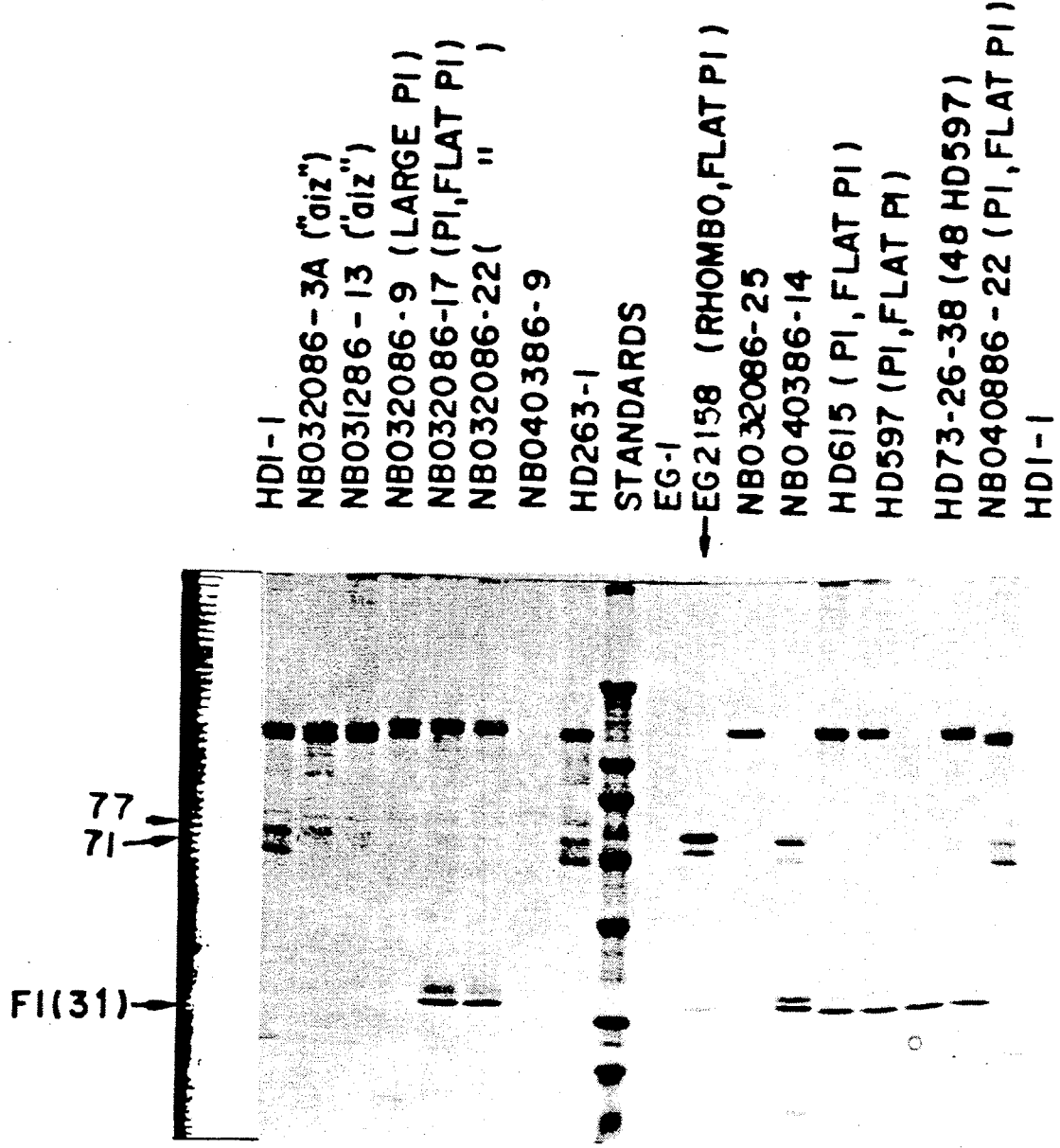

FIG. 4 is a photograph of a gel electrophoresis showing a comparison of the crystalline proteins from EG2158 to other strains producing the F-1 (flat pI) crystal. The arrows indicate proteins made by EG2158. NB number indicates new Bacillus isolate.

Figure 5A:
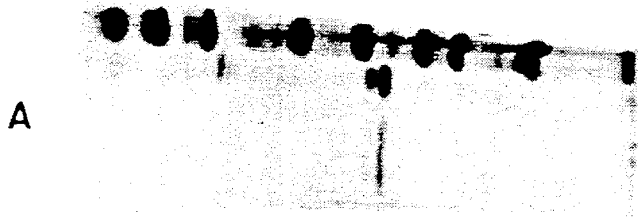
Figure 5A:
Figure 5B:

FIG. 5 is comprised of 5(A), 5(A') and 5(B'). 5(A) is a photograph of a gel electrophoresis of the R-1 and F-1 crystal proteins. 5 (A ) and 5(B') are also photographs of electrophoresis gels which show the differential production of 77 and 71 kDa proteins in EG2158 and derivatives of EG2158.

FIG. 6 is comprised of 6(A) and 6(B), both of which are photographs of a gel electrophoresis showing the productions of the 71 kDa protein in transconjugant strains having the 88-Md plasmid from EG2158.

Figure 7A:
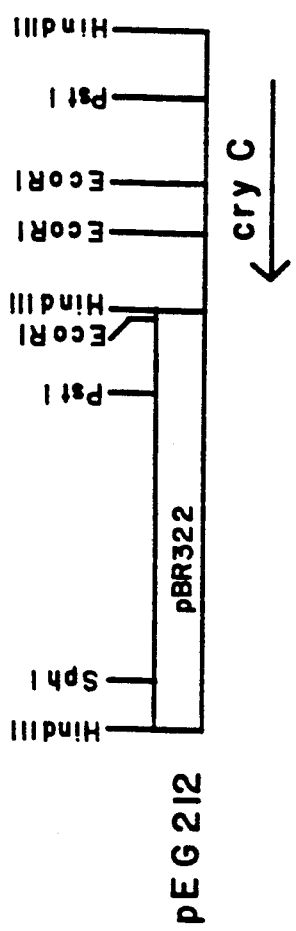
Figure 7B:
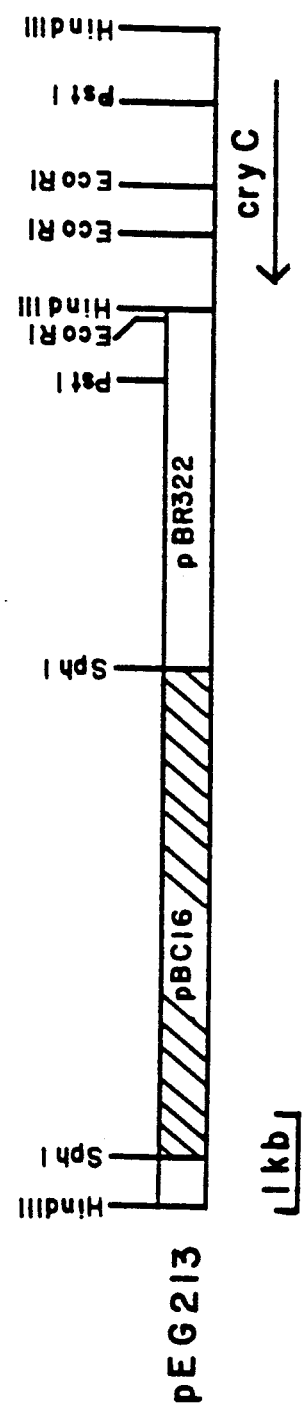

FIG. 7 consists of 7(A) and 7(B) which depict respectively restriction maps is a restriction map of the recombinant plasmids pEG212 and pEG213 that contain the cloned cryC gene. The location and direction of transcription of the cryC gene are indicated by the large arrow.

FIG. 8 shows the DNA sequence of the cryC gene (including nucleotides 569 to 2500 which code for the structural toxin protein and nucleotides 2501–2503 code for the "stop" signal) and also the amino acid sequence of the coleopteran toxin encoded by the cryC gene (nucleotides 569–2500).

FIG. 9 is comprised of 9a and 9b. 9a is a photograph of an ethidium bromide stained Eckhardt gel. The native plasmids that are present in Bacillus thuringiensis strains HD1 and EG2158 are visible illustrating that certain B.t. strains contain several native plasmids. 9b is a photograph of an autoradiogram that was made by hybridizing the radioactively labeled cloned cryC gene with the plasmids shown in 9a 9b illustrates that the cloned cryC gene hybridized exclusively to a plasmid of 88 MDa in the coleopterantoxin strain EG2158 but failed to hybridize to any plasmids in strain HD1, a strain that is not toxic to coleopterans.

Figure 10:
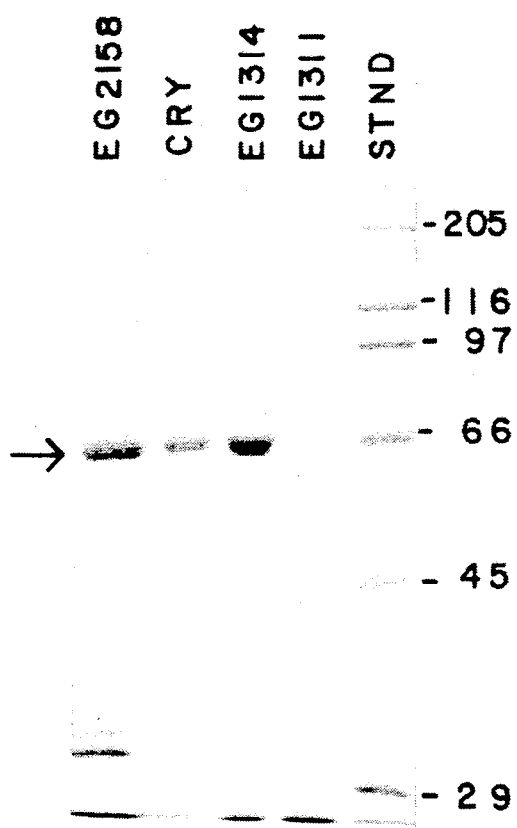

FIG. 10 is a photograph of an SDS/polyacrylamide gel which shows that a recombinant host strain of Bacillus megaterium (EG1314) harboring the cloned cryC gene synthesizes large quantities of a protein having a size similar to that of authentic coleopteran (cry) toxin.

5.0 DESCRIPTION OF THE INVENTION

Generally stated, the present invention provides a newly isolated Bacillus thuringiensis strain which has insecticidal activity against insects of the order Coleoptera. A biologically pure culture of this strain has been deposited with the NRRL. Bioassays described below have confirmed the coleopteran activity of this strain. This strain of B.t., therefore, is preferred for use as at least one of the active ingredients in an insecticide composition useful against coleopteran insects.

The present invention further provides for transconjugant derived Bacillus thuringiensis strains which have insecticidal activity against both lepidopteran and coleopteran insects. This dual activity in B.t. is unknown in the wild. A B.t. strain having this dual activity would also, therefore, be preferred for use as at least one of the active ingredients in an insecticide composition useful against both coleopteran and lepidopteran insects.

Additionally, this invention provides, generally stated, a method for producing Bacillus thuringiensis strains having insecticidal activity against both coleopteran and lepidopteran insects comprising:

(a) providing a Bacillus thuringiensis strain having insecticidal activity against coleopteran insects conferred by a gene coding for coleopteran active toxin protein said gene being located on a plasmid said strain being in admixture with a Bacillus thuringiensis strain having insecticidal activity against lepidopteran insects under conditions favoring conjugation and (b) isolating from the culture admixture of step (a) a transconjugant having activity against both lepidopteran and coleopteran insects.

This method, in a preferred embodiment, also utilizes intermediate strains to transfer either the coleopteran or lepidopteran toxin-coding plasmid to another intermediate recipient strain or directly to the ultimately desired transconjugant host which already would contain at least one other of the toxin encoding plasmids.

The general method described above also encompasses the embodiment wherein said Bacillus thuringiensis strain of step (a) having activity against coleopteran insects additionally has activity against lepidopteran insects conferred by at least one gene coding for a lepidoperan-active toxin, whereby said transconjugant of step (b) has lepidopteran and coleopteran activity conferred by at least three toxin genes.

The general method described above additionally encompasses the embodiment wherein said *Bacillus thuringiensis* strain of step (a) has activity against lepidopteran insects conferred by more than one toxin gene, whereby said transconjugant of step (b) has lepidopteran and coleopteran activity conferred by at least three toxin genes.

For instance, in the practice of this invention a strain having coleopteran activity would be provided in admixture first with a *Bacillus thuringiensis* strain whereby said *Bacillus thuringiensis* strain acquires (by conjugation) the plasmid conferring insecticidal activity against Coleoptera and then providing the transconjugant strain in admixture with said *Bacillus thuringiensis* having lepidopteran activity under conditions favoring conjugation whereby said *Bacillus thuringiensis* strain having lepidopteran activity acquires the plasmid conferring coleopteran activity by conjugation from said transconjugant strain.

The present invention also provides for a cloned gene coding for *Bacillus thuringiensis* coleopteran active toxin comprising the DNA nucleotide sequence shown in FIG. 8. This gene (which comprises double stranded DNA wherein the nucleotide strands have a complementary base sequence to each other) codes for a protein (or as also used herein equivalently, polypeptide) having the amino acid sequence of the coleopteran active toxin which amino acid sequence is shown in FIG. 8. The coleopteran active toxin encoded by the cloned gene has insecticidal activity against coleopteran insects.

Methods of producing the coleopteran active protein are also provided by this invention. In this method of production the cryC gene is inserted into a cloning vector or plasmid which plasmid is then utilized to transform a selected microorganism.

The cloning vectors, as described herein, are generally known in the art and are commercially available. The choice of a particular plasmid is within the skill of the art and would be a matter of personal choice. Plasmids suitable for use in this invention are, for instance, pBR322, plasmids derived from B.t., and plasmids derived from *Bacillus* and *Staphylococcus* microorganisms, preferrably, *Bacillus megaterium*. Microorganisms suitable for use with this invention are both sporulating and non-sporulating microorganisms such as *E. coli*, B.t., and *Bacillus megaterium*. The microorganisms utilized are also known in the art and are generally available. The choice of any particular microorganism for use in the practice of this invention is also a matter of individual preference. In a preferred embodiment of this invention the microorganism would comprise *Bacillus megaterium*.

Generally stated, the coleopteran active toxin protein can be produced by a transformed organism and later purified into a homogenous preparation having an amino acid sequence as shown in FIG. 8. More specifically, this protein may be produced by transforming a microorganism with a plasmid containing the cryC gene, growing the transformed microorganism so that the protein coded for by the cryC gene is expressed in the microorganism and by extracting the protein from the organism with standard protein purification techniques. It is also within the scope of this invention that the protein not be separated from the transformed microorganism but that this organism, including the expressed coleopteran active protein, be utilized as or in an insecticidal composition.

This invention also provides for a novel insecticide for use against Coleoptera comprising a mixture of B.t. coleopteran active toxin and a suitable carrier. The toxin may be contained in the organism or associated with spores, or be a homogeneous protein preparation or in a mixture of spores with cultured transformed organisms. The toxin may also be contained in a non-sporulating microorganism or a sporulating microorganism such as *Bacillus megaterium* or B.t. A suitable carrier may be any one of a number of solids or liquids known to those of skill in the art.

This invention also comprises the recombinant vectors or plasmids including the cryC gene and the particular microorganisms which have been transformed with this gene. In addition, this invention also provides for oligonucleotide probes for the gene coding for the coleopteran active delta-endotoxin. All of these aspects of the inventions are described in detail below and illustrated in the following examples.

5.1 Coleopateran Active *Bacillus thuringiensis*

EG2158 is a B.t. strain isolated (deposited and maintained as a biologically pure culture) from soybean grain dust from Kansas. EG2158 produces two types of intracellular inclusion during sporulation (FIG. 1): A somewhat rhomboid crystal (referred to below as R1) and a flat, diamond-shaped crystal (referred to below as F1). Bioassays set forth in the Examples below show that sporulated cultures of EG2158 (consisting of a mixture for spores, R1 and F1 crystals) were toxic to larvae of the Colorado potato beetle (hereinafter alternatively referred to as CPB.), *Leptinotarsa decemlineata* (Say), but not toxic to lepidopteran larvae of several species (*Trichoplusia ni* and others).

EG2158 contains a unique plasmid array (FIG. 2) of 5 plasmids of approximate sizes of 35, 72, 88, 105 and 150 megadaltons (Md).

Table I below describes which plasmid codes for a particular toxin.

TABLE I

| STRAIN EG2158 COLEOPTERAN ACTIVITY IS ENCODED BY A TRANSMISSIBLE PLASMID | |
|---|---|
| TOXIN PLASMID | PROPERTIES |
| 150 Md | Encodes "flat diamond" crystal. Loss has no effect on coleopteran activity. |
| 88Md | Encodes rhomboid crystal and coleopteran activity. Transfers into B.t. and *B. cereus* recipient strains. Transconjugant made rhomboid crystal and is toxic to CPB larvae. |

Loss of the 150 Md plasmid eliminated production of F1 crystal without affecting toxicity to CPB, while loss of the 35Md plasmid had no effect on R1 or F1 production or toxicity. (Table II)

(Strains of EG2158 and its variants, and all B.T. and *B. Cereus* strains were grown for bioassay as follows: spores were inoculated into 5 mls of M27 broth in a 50 ml sterile flask. M27 broth is composed of 33 mM each of $HPO_4=$ and $H_2PO_4-$ anions; 98 mM $K^+$; 0.17% peptone; 0.1% beef extract; 150 mM NaCl; 5.5 mM glucose; 330 uM $Mg^{++}$, 230 uM $ca^{++}$, and 17 uM $Mn^{++}$ (added as the chloride salts). (As used herein, the letter "u" when used as part of a term of measurement or quantity is synonomous with the prefix "micro".) The cultures were incubated at 30° C. with shaking for 3 days, at which time sporulation and crystal formation were complete. Five ul of sterile 1-octanol were added as an anti-foaming agent and the cultures were transferred to sterile plastic tubes, sealed, and stored at 5° C.)

TABLE II

Mortality and leaf consumption by first instar Colorado Potato Beetle larvae on potato leaf discs treated with BT

| Strain | Number Alive /10 at 24 h | 48 h | Approximate Leaf Consumption % |
|---|---|---|---|
| (Control) | 10 | 10 | 90 |
| 1 EG2158 | 10 | 2 | 10 |
| 2 EG2158 (−150 Md; - flat diamond (F-1)) | 10 | 1 | 15 |

When EG2158 was grown in mixed culture with other strains of B.t. or *B. cereus*, the 105- and 88Md plasmids were transmitted, by conjugation, into the other strians. B.t. or *B. cereus* strains which acquired the 105-Md plasmid were not altered detectably (that is, the 105-Md plasmid is transmissible but otherwise cryptic). B.t. or *B. cereus* strains which acquired the 88-Md plasmid were seen to produce R1 crystals. Therefore, it was discovered that the 88-Md plasmid is transmissible and encodes R1 crystals, and yields transconjugant strains which are R1 producers. The plasmid arrays of some R1-producing transconjugants are shown in FIG. 3.

TABLE III

TRANSCONJUGANTS HARBORING COLEOPTERAN AND LEPIDOPTERAN-ACTIVE TOXIN PLASMIDS

| TRANS-CONJUGANT | TOXIN PLASMID (Source strain) | TOXIN PLASMID TARGET INSECTS |
|---|---|---|
| HD73-26-46 | 88 (EG2158) | CPB |
| HD73-26-50 | 88 (EG2158) | CPB |
| | 44 (HD-263) | LEP |
| HD73-26-54 | 88 (EG2158) | CPB |
| | 61 (HD-617) | LEP |
| HD73-26-56 | 88 (EG2158) | CPB |
| | 50 (HD-78) | LEP |
| | 54 (HD-2) | LEP |
| | 75 (HD-2) | LEP |
| BC569-6-15 | 88 (EG2158) | CPB |
| | 68 (HD-536) | UNK |
| HD1-10-1 | 88 (EG2158) | CPB |
| HD263-8-5 | 88 (EG2158) | CPB |
| | 60 (HD-263) | LEP |

The 88-Md plasmid was put into recipients of three B.t. backgrounds (HD-73, HD-1, and HD-263) and one of *B. cereus* origin (BC-569). The 88-Md plasmid was shown to coexist with toxin plasmids encoding lepidopteran (P1) toxin crystals, such as the 44-Md toxin plasmid from HD263, and others (See FIG. 3 and Table III). Transconjugants producing R1 crystals were toxic to CPB, as was EG2158 (Table IV, A and B) and were also toxic to lepidopteran larvae (Table V, A and B).

TABLE IV

A. MORTALITY AND LEAF CONSUMPTION BY FIRST INSTAR COLORADO POTATO BEETLE LARVAE ON POTATO LEAF DISCS TREATED WITH *Bacillus thuringiensis*

| Strain | Phenotype | Number Alive/10 at 24 h | Number Alive/10 at 48 h | Approx. Leaf Consumption (%) |
|---|---|---|---|---|
| (Control) | | 10 | 9 | 80 |
| HD73-26-46 | Rhomboid+: 88+ <EG2158 | 5 | 0 | 5 |
| HD73-26-47 | Rhomboid+: 88+, 105 <EG2158 | 6 | 3 | 5 |
| HD73-26-48 | Osp. Rhomboid+: 88+ <EG2158 | 4 | 2 | 5 |
| HD73-26-49 | Osp. Rhomboid+: 88+, 105 <EG2158 | 1 | 0 | 5 |
| HD73-26-50 | Rhomboid+, Pl+: 88+, 105 <EG2158; 44+ <HD263 | 5 | 0 | 5 |
| HD73-26-51 | Rhomboid+, [Pl]+: 88+, 105 <EG2158; [54]+ <HD2 | 2 | 2 | 5 |
| HD73-26-52 | Rhomboid+, Pl+: 88+, <EG2158; 75+ <HD2 | 2 | 2 | 5 |
| HD73-26-53 | Rhomboid+, Pl+: 88+, 105 <EG2158; 75+ <HD2 | 1 | 0 | 5 |
| HD73-26-54 | Rhomboid+, Pl+: 88+ <EG2158; 61+ <HD617 | 5 | 2 | 5 |
| HD73-26-55 | Rhomboid+, Pl+: 88+, 105 <EG2158; 61+ <HD617 | 6 | 1 | 10 |
| BC569-6-14 | Rhomboid+: 88+ <EG2158; | 4 | 1 | 5 |
| HD73-26 | Cry− control | 10 | 1 | 60 |
| HD73-26-56 | Rhomboid+, Pl+: 88+ <EG2158; 75+, [54]+ <HD2; 50+ <HD78 | 8 | 0 | 20 |
| HD73-26-57 | Rhomboid+, Pl+: 88+, 105 <EG2158; 75+, [54]+ <HD2; 50+ <HD78 | 5 | 1 | 5 |
| BC569-6-15 | Rhomboid+, Round+: 88+, 105+ <EG2158; 68+ <HD536 | 7 | 1 | 10 |
| HD1-10-1 | Rhomboid+: 88+, <EG2158; | 8 | 1 | 10 |
| HD263-8-5 | Rhomboid+, Pl+: 88+, <EG2158; 60+ (native) | 5 | 1 | 10 |

B. BIOASSAY AGAINST COLORADO POTATO BEETLE

| Strain | Dose μg/cup | Mortality % dead | |
|---|---|---|---|
| EG2158 | 1770 | 100 | |
| | 177 | 80 | |
| | 17.7 | 20 | PLC50 = 55 |
| HD263-8-72 | 2340 | 10 | |
| | 234 | 30 | |

TABLE IV-continued

|  | 23.4 | 20 |  |
| --- | --- | --- | --- |
| HD263-8-73 | 2450 | 100 |  |
|  | 245 | 50 | PLC50 = 185 |
|  | 24.5 | 10 |  |
| Control mortality 10%. | | | |

HD263-8-72 contains the same lepidopteran-active plasmids as HD263-8-73, but lacks the 88+ Md coleopteran-active plasmid.

TABLE V

A. ACTIVITY OF TRANSCONJUGANTS WITH COLEOPTERAN TOXICITY AGAINST *OSTRINIA NUBILALIS* (LEPIDOPTERA)

| Liquid Culture | Strain | Donor Plasmid | Pug/ ml | No. of Tests | PLC50 |
| --- | --- | --- | --- | --- | --- |
| MB 96 | HD263-8-73 | 44+ <HD279 | 245 | 3 | 14.2 |
| AK 3 | HD263-8-6 | 50+ <HD73 | 252 | 3 | 20.4 |
| AK 4 | HD263-8-7 | 46+ <HD122A | 260 | 4 | 20.5 |
| AK 5 | HD263-8-8 | 50+ <HD119 | 238 | 3 | 13.3 |
| AK 6 | HD263-8-9 | 50+ <HD78 | 233 | 4 | 11.2 |
| AK 7 | HD263-8-10 | 66+ <HD588 | 247 | 4 | 27.4 |
| AK 8 | HD263-8-11 | 54, 52 <HD206A | 258 | 4 | 8.8 |
| AK 9 | HD263-8-12 | [47]+ < NB-032786-1C | 258 | 4 | 10.1 |

B. ACTIVITY OF HD 263-8-5 AGAINST VARIOUS LEPIDOPTERA

| | HD 263-8-5 | | HD 1-1 | |
| --- | --- | --- | --- | --- |
| Insect | Dose | % dead | Dose | % dead |
| *Heliothis virescens* | 25 | 60 | 28 | 80 |
| *Heliothis zea* | 377 | 30 | 419 | 70 |
| *Spodoptera exigua* | 377 | 10 | 419 | 80 |
| *Lymantria dispar* | 38 | 50 | 42 | 80 |

All strains also have the 88+Md plasmid from EG2158, as well as the 60+Md P1 toxin plasmid native to HD-263.
Dosage is in nanograms crystal protein per diet cup as a surface treatment.

Transconjugants producing both R1 and P1 toxin crystals were shown to be toxic to both CPB and lepidopteran larvae. Their production is described in detail below.

Proteins from the EG2158 crystals, R1 and F1, run on PAGE were determined to be 77,71 and 31 kDa (see FIG. 4). The R1 crystals were shown to be soluble in 4M NaBr (FIG. 5(A) ("NaBr sup"), leaving the F1 crystals (FIG. 5(A) "NaBr ppt"). This allowed assignment of the 77 kDa and 71 kDa proteins to the R1 crystal (FIG. 5(A)). Recrystallized R1 proteins were toxic to CPB larvae. In certain media and strain backgrounds the 71 kDa protein is produced exclusively (FIG. 5(A') and (B')). FIG. 5 shows the differential production of 77 and 71 kDa proteins in derivatives of EG2158 on same medium (A') and differential production by one derivative (minus F1) on different media(B'). The extra band at 32 kDa (above F1) is probably a proteolytic fragment of R1.

When the 88-Md plasmid from EG2158 was transferred to other B.t. backgrounds (using the EG2158 culture "O-24" as the source of donor cells), the 71 kDa protein was produced (FIG. 6). These strains are also toxic to CPB. Expression of coleopteran toxin (R1) in *kurstaki* transconjugants and in *B. cereus* is undiminished in the presence of other toxin plasmids. The presence of the coleopteran toxin plasmid does not inhibit production of other (e.g. lepidopteran) toxins; nor does it induce the production of toxin by conditional plasmids.

In a preferred embodiment, spores should be included with either EG2158 or other strains harboring the coleopteran toxin plasmid in order to achieve maximum insecticidal activity. These can be spores of the original strain, or spores from another strain.

Southern blotting experiments have shown that a 0.7 kilobase EcoR1 DNA fragment homologous to P1 (lepidopteran) toxin genes does not hybridize to any DNA sequences in EG2158.

5.2 Transconjugants Having Coleopteran and Lepidopteran Activity

In a preferred embodiment of this invention *Bacillus thuringiensis* strains which have insecticidal activity against both lepidopteran and coleopteran insects may be generated by conjugation. To date, *Bacillus thuringiensis* strains having this dual activity are unknown in the wild.

Generally stated and as noted above, this invention also provides a method for producing *Bacillus thuringiensis* strains having insecticidal activity against both coleopteran and lepidopteran insects comprising:

(a) providing a *Bacillus thuringiensis* strain having insecticidal activity against coleopteran insects in admixture with a *Bacillus thuringiensis* strain having insecticidal activity against lepidopteran insects under culture conditions favoring conjugation and (b) isolating from the culture admixture of step (a) a transconjugant having activity against both lepidopteran and coleopteran insects.

This method in a preferred embodiment also utilizes intermediate strains (not having toxin-encoding plasmids) to transfer either the coleopteran or lepidopteran toxin-coding plasmid to another intermediate recipient strain or directly to the ultimately desired transconjugant host (which already would preferably contain at least one other of the toxin-encoding plasmids).

More specifically, these transconjugant strains may all be generated according to the following procedure.

A BT strain such as EG2158 would be used as a donor by growing it together with an recipient strain, such as HD73-26. All plasmid transfers would be carried out by inoculating spores of donor and recipient strains into M27 broth (or other media suitable for B.t. growth) and allowing the strains to grow together for 6 or more hours at 30.C, with gentle shaking. Afterwards, colonies of the recipient strain would be selected for by using streptomycin-containing plates (in the case of HD73-26, which is resistant to streptomycin) or would be identified by random screening. In some cases, nutrient media other than M27 broth may be used. In this manner, a transconjugant would be created, which would have acquired plasmids from EG2158. The transconjugant would then be used as a donor by growing it and a second recipient strain having toxin plasmids to Lepidoptera together in liquid broth. The resulting transconjugant would have acquired the 88+Md plasmid from EG2185 which includes the gene for the Coleoptera active toxin (confirmed by plasmid array gel electrophoresis).

The 88-Md coleopteran toxin plasmid of EG2158 was transferred by conjugation into HD263-8 (a recipient BT strain containing a native lepidopteran toxin plasmid, 60 Md in size) to give the transconjugant HD263-8-5 (EG2421), which produces both lepidopteran (P1) and coleopteran (rhomboid) toxin crystals. In a similar manner, the 44-Md lepidopteran toxin plasmid of HD279 was transferred to the crystal-negative strain HD73-26 to give the transconjugant HD73-26-73. HD263-8-5 was then used as recipient and HD73-26-73 was used as a donor. The resulting transconjugant, HD263-8-73 (EG2424), has acquired the 44-Md (P1) toxin plasmid of HD-279, via the intermediate donor strain HD73-26-73. HD263-8-73 (EG2424) contains 3 toxin plasmids - the 88-Md coleopteran toxin plasmid from strain EG2158, and the 60 and 44 Md lepidopteran toxin plasmids from strains HD263-8 and HD279 respectively. The resulting strain (EG2424) is active against both Coleoptera (Table IVB) and Lepidoptera (Table VA), unlike any of the starting strains EG2158, HD263-8, or HD279. Furthermore, the activity of this strain (amount of P1 toxin) against Lepidoptera is greater than that of strain HD263-8-5.

5.3 Recombinant DNA Technology and Gene Expression

Generally stated, recombinant DNA technology as used in the practice of this invention involves insertion of specific DNA sequences into a DNA vehicle (plasmid or vector) to form a chimeric DNA molecule which is capable of replication in a host cell. The inserted DNA sequence is typically foreign to the recipient host, i.e, the inserted DNA sequence and the DNA vector are derived from organisms which do not exchange genetic information in nature, or the inserted DNA sequence may be wholly or partially synthetically made. In recent years several general methods have been developed which enable construction of recombinant DNA molecules, For example, U.S. Pat. No. 4,237,224 to Cohen and Boyer describes production of such recombinant plasmids using restriction enzymes and methods known as ligation. These recombinant plasmids are then introduced and replicated in unicellular organisms by means of transformation. Because of the general applicability of the techniques described therein, U.S. Pat. No. 4,237,224 is hereby incorporated by reference into the present specification.

Regardless of the method used for construction, the recombinant DNA molecule must be compatible with the host cell, i.e., capable of autonomous replication in the host cell. The recombinant DNA molecule should also have a marker function which allows the selection of host cells so transformed by the recombinant DNA molecule. In addition, if all of the proper replication, transcription and translation signals are correctly arranged on the chimeric DNA molecule, the foreign gene will be expressed in the transformed cells and their progeny.

These different genetic signals and processing events control many levels of gene expression, i.e., DNA transcription and messenger RNA translation. Transcription of DNA is dependent upon the presence of a promoter which is a DNA sequence that directs the binding of RNA polymerase and thereby promotes transcription.

Translation of messenger RNA (mRNA) in procaryotes depends upon the presence of the proper procaryotic signals. Efficient translation of mRNA in procaryotes, such as B.t., requires a ribosome binding site on the mRNA. This sequence is a short nucleotide sequence of mRNA that is located before the start codon (AUG) which encodes the amino-terminal methionine of the protein. The ribosome binding site is complementary to the 3'-end of the 16S RNA (ribosomal RNA) and probably promotes binding of mRNA to ribosomes by duplexing with the mRNA to allow correct positioning of the ribosome (Roberts and Lauer, 1979, Methods in Enzymology, 68:473).

One method widely employed for the cloning of a particular gene is to prepare a "library" of recombinant plasmids. Each recombinant plasmid is comprised of a plasmid vector, which usually confers antibiotic resistance to cells that harbor it, plus a fragment of DNA from the donor organism, an organism that contains the gene. The plasmid library is commonly prepared by digestion of both the plasmid vector and total DNA from the donor organism with a restriction enzyme, inactivation of the enzyme and ligation of the DNA mixture. The ligated DNA is a plasmid library. The key feature of this plasmid library is that it contains many different recombinant plasmids. It is highly likely that at least one of the recombinant plasmids in the library will contain a fragment of DNA from the donor organism on which the gene of interest resides. The plasmid library is transformed into the cells of a host organism that does not contain the gene. The host cells are spread on a selective solid medium, usually one containing an antibiotic, that allows only transformed cells, those containing recombinant plasmids, to grow into colonies. Individual transformed host colonies are tested for the acquisition of the gene from the donor organism. In host colonies the acquired gene is carried on the recombinant plasmid.

One of the most direct methods of testing for the acquisition of a gene is to use a gene-specific hybridization probe, a fragment of DNA that is homologous to the gene. A characteristic of homologous DNA fragments is that they will bind tightly to each other during hybridization. Typically a radioactively labeled DNA probe is used during hybridization so that binding of the probe to the gene can be easily monitored.

A recent advance in molecular biology is the use of synthetic oligonucleotides as gene-specific probes. The basis for the use of the oligonucleotides is that in all biological systems a particular sequence of nucleotides encodes a precise sequence of amino acids. Conversely if the sequence of amino acids is known for a particular protein then the nucleotide sequence encoding the protein can be inferred, although not precisely. In practice, the partial amino acid sequence of a protein, the product of the gene of interest, is determined by chemical methods. Based on the protein amino acid sequence a gene-specific oligonucleotide probe is synthesized that may be, to varying degrees, homologous to the gene. Exact homology cannot be guaranteed because knowledge of the amino acid sequence of a protein does not give exact knowledge of the nucleotide sequence of the gene encoding the protein. Nevertheless, even though the homology between the oligonucleotide probe and the gene may not be precise, hybridization conditions can usually be found that will permit the oligonucleotide probe to bind specifically to the gene.

Accordingly, in isolating the cryC gene, the coleopteran toxin was purified from the *B. thuringiensis* strain EG2158, and the partial amino acid sequence of the coleopteran toxin was determined. A cryC gene-specific oligonucleotide probe was synthesized based on the amino acid sequence of the coleopteran protein. The oligonucleotide was radioactively labeled and was used in hybridization experiments to identify transformed host colonies that harbored recombinant plasmids carrying the cryC gene from the donor B.t. strain.

5.4 Cloning of the cryC Toxin Gene From *Bacillus thuringiensis* Strain EG2158

More specifically, in order to clone the cryC toxin gene of this invention, cells of B.t. strain EG2158 were grown in C2 media (1% Glucose, 0.2% Peptone, 0.5% N Z Amine A, 0.2% Yeast Extract, 15 mM (NH$_4$)$_2$SO$_4$, 23 mM KH$_2$PO$_4$, 27 mM K$_2$HPO$_4$, 1 mM MgSO$_4$·7H$_2$O, 600 uM CaCl$_2$, 17 uM ZnSO$_4$·7H$_2$O, 17 uM CuSO$_4$·5H$_2$O, 2 uM FeSO$_4$·7H$_2$O) at 30° C. until t72 (hours) and spores plus crystals were harvested by centrifugation. The spore/crystal pellet was washed with several changes of 1 M NaCl and then several changes of deionized water. Toxin proteins were solubilized by incubating the spore/crystal preparation in 5% beta-mercaptoethanol, 2% NaDodeSO4, 60 mM Tris pH 6.8, 10% glycerol at 70 degrees C. for 7 min., and spores were removed by centrifugation. The supernatant was electrophoresed through polyacrylamide gels containing NaDodeSO4 to separate proteins. The gel was stained with Coomassie dye and gel slices containing the coleopteran active protein were cut out with a razor blade. The homogeneous coleopteran active protein preparation was electroeluted from gel slices and, after acetone precipitation, the NH2-terminal amino acid sequence of the coleopteran active protein was determined by automated Edman degradation carried out on an Applied Biosystems Gas Phase Sequenator (model 470A) and analyzed on a DuPont Zorbax C18 column in a Hewlett-Packard HPLC (model 1090) with a 1040 diode array detector. The NH$_2$-terminal amino acid sequence of the 71 kDA coleopteran toxin has been determined to be:

1
NH2— ASP GLU ALA LEU THR SER SER THR ASP LYS

11
ASP VAL ILE GLN LYS GLY ILE SER VAL VAL

22
ILE ASP LEU LEU

It is significant that Edman sequencing of the 71 kDa coleopteran toxin revealed no NH2-terminal methionine residue. We believe that the 71 kDa coleopteran toxin is a processed form of a larger precursor protein of about 77 kDa. The evidence for this is as follows. Occasionally on SDS/polyacrylamide gels a protein of 77 kDa was seen in addition to the 71 kDa protein from cell extracts of strain EG2158. If the cell extracts were incubated at 55° C. rather than 70° C. none of the 77 kDa protein was seen. At 55° C. B.t. proteases would not be completely inactivated. Protease activity is probably responsible for processing of the 77 kDa protein into the 71 kDa form. Since no NH2-terminal methionine residue was seen in the 71 kDa protein we conclude that proteases indigenous to B.t. cleave off approximately 5kDa, or 50 amino acids, from the NH2-terminus of the 77 kDa protein to yield the 71 kDa processed protein.

5.5 Oligonucleotide Probe for the cryC Gene

An oligonucleotide probe encoding amino acids 1 through 22 of the NH2-terminus of the coleopteran active protein was synthesized on an Applied Biosystems DNA synthesizer (model 380A). It was recognized that because of the codon degeneracy (certain amino acids are each encoded by several slightly different codons) the sequence of the synthetic oligonucleotide would probably be different from the actual NH2-terminal sequence of the cryC gene. However, the fact that the B.t. genome is 68% A+T and the codon usage information for previously cloned and sequenced B.t. genes were used in designing an oligonucleotide probe that would have the highest probability of matching the actual sequence of the cryC gene. The oligonucleotide probe was designed to bind only to the NH2-terminal coding region of the cryC gene. The sequence of the cryC gene-specific oligonucleotide probe was:

5'-GAT GAA GCA TTA ACA TCA TCA ACA
   GAT AAA GAT GTA ATT CAA AAA GGA
   ATT TCA GTA GTA ATT GA-3'

In addition to enabling the original isolation of the cryC gene herein, this DNA probe also comprises another preferred embodiment of this invention. This DNA probe permits the screening of any B.t. strain to determine whether the cryC gene (or possibly a related gene) is naturally present or whether a particular transformed organism includes the cryC gene. In this fashion it is also possible to estimate the insecticidal activity of that strain of B.t. It is also with the scope of this invention that this probe may comprise a smaller or larger oligonucleotide or another region of the gene. The probe may be labeled by any number of techniques known in the art (such as radioactively or enzymatically labeled) and as described below.

5.6 Construction of a Plasmid Library Enriched for the cryC GENE

The oligonucleotide probe was used to determine the size of a restriction fragment of B.t. DNA that contained at least the NH2-terminal coding region of the cryC gene. For this determination strain EG2158, the coleopteran toxic strain, was used as a source of DNA. B.t. strain HD1-1, a single colony isolate immediately derived from parent strain HD-1 (U.S.D.A., Brownsville, Tex.) was used as a control.

DNA was isolated from the donor strain EG2158 after growth of the cells to mid-log phase at 30° C. in LB medium. Cells were harvested by centrifugation, resuspended in 50mM Tris HCl pH 7.8, 10mM EDTA, 1 mg/ml lysozyme and incubated at 37° C. for 60 min. Cells were lysed by adding NaDodeSO4 to a final concentration of 0.2%. Cell lysates were extracted twice with an equal volume of phenol and once with an equal volume of chloroform/isoamyl alcohol (24/1). One tenth volume of 3 M NaAcetate and 2 volumes of EtOH were added to the lysates and DNA was extracted by spooling on a glass rod. The spooled DNA was soaked in 66% EtOH for 5 min. and in diethyl-ether for 1 min. The spooled DNA was air dried and resuspended in deionized water.

Hybridization experiments were performed by digesting total DNA from each of the donor strains with HindIII restriction enzyme, electrophoresing the digested DNA on an agarose gel and transfering the DNA from the agarose gel to a nitrocellulose filter by the blot technique of Southern (J. Molec. Biol. 98:503–517, 1978). The nitrocellulose filter was incubated at 32° C. for 16 hrs. in a solution of 3×SSC (1×SSC=0.15M NaCl/0.015 M Sodium Citrate), 0.1 % NaDodeSO4, 200 ug/ml heparin, 10 X Denhardt's (1×=0.02% Bovine Serum Albumin/0.02% Ficoli/0.02% Polyvinyl-Pyrrolidone) containing approximately 1 ug of the cryC gene-specific oligonucleotide probe that had been radioactively labeled with gamma-P32-ATP and T4 kinase. After hybridization the nitrocellulose filter was washed with 3×SSC, 0.1 % NaDodeSo4 at 47° C. for one hour and the filter was exposed to X-ray film. The resulting autoradiogram showed that the oligonucleotide probe specifically hybridized to a single Hind III fragment of 2.6 Kb from strain EG2158 but failed to hybridize to any fragments from the coleopteran toxin-negative control HD1-1.

A cryC-enriched plasmid library was constructed by digesting EG2158 total DNA with HindIII, electrophoresing the digested DNA on an agarose gel and excising gel slices containing HindIII DNA fragments ranging in size from approximately 2.0 to 3.0 kb. EG2158 HindIII fragments ranging in size from 2.0 to 3.0 kb Were electroeluted from agarose gel slices, phenol plus chloroform extracted, ethanol precipitated and ligated into the HindIII site of plasmid pBR322 that had been digested with HindIII and treated with alkaline phosphatase. Alkaline phosphatase greatly increased the probability that recombinant plasmids were formed consisting of pBR322 plus a HindIII fragment of EG2158 DNA. The resulting ligation mix consisted of a library of recombinant plasmids enriched for the cryC toxin gene from strain EG2158.

5.7 Colony Hybridization and Isolation of A 2.6 kb HindIII Fragment Containing the cryC Gene The cryC gene-enriched plasmid library was transformed into an ampicillin sensitive host strain of *E. coli*, HB101 (Bethesda Research Laboratories, Bethesda, Md.), by the CaCl2 procedure. *E. coli* strain HB110does not synthesize coleopteran toxin protein and, therefore, it would not be expected to contain the cryC gene. *E. coli* was used as the host strain because these cells are easily transformed with recombinant plasmids. All host cells acquiring a recombinant plasmid would become ampicillin resistant. After exposure to the recombinant plasmids the *E. coli* host cells were spread onto solid medium containing ampicillin and those cells that harbored a recombinant plasmid were able to grow into colonies. It was expected that each individual ampicillin resistant host colony would harbor many identical copies of a recombinant plasmid comprised of pBR322 plus a unique HindIII fragment from the donor strain EG2158 DNA. However, the donor strain HindIII fragment in the recombinant plasmid would differ from one colony to the next.

Approximately two thousand individual ampicillin resistant colonies were blotted onto nitrocellulose filters. Replicas of the colonies were saved for later use as described below. The recombinant plasmids contained in the colonies were bound to the nitrocellulose filters by treating the colonies with NaOH and $NH_4$Acetate. The resulting nitrocellulose filters contained an array of recombinant plasmids each of which was physically separated from other recombinant plasmids. The nitrocellulose filters were hybridized at 50° C. for 16 hours in a solution of 3×SSC, 200 ug/ml heparin, 0.1% NaDodeSO$_4$, 10×Denhardt's and approximately 1 ug of the cryC gene-specific oligonucleotide probe that had been radioactively labeled. The filters were washed at 47° C. for one hour in 3×SSC, 0.1% NaDodeSO$_4$ and were exposed to x-ray film. The resulting autoradiogram showed that the oligonucleotide probe had hybridized to twelve different locations on the nitrocellulose filters.

By aligning the autoradiogram with the colony replicas it was possible to identify twelve colonies whose recombinant plasmids had apparently hybridized with the oligonucleotide probe.

Plasmids were extracted from each of the twelve colonies. The plasmids were digested with HindIII and electrophoresed on an agarose gel. The plasmids were transferred from the agarose gel to a nitrocellulose filter by the blot procedure of Southern. The nitrocellulose filter was hybridized with the radioactively labeled oligonucleotide probe and exposed to x-ray film. The resulting autoradiogram showed that the oligonucleotide probe hybridized exclusively to a 2.6 kb HindIII fragment that was contained in only one of the twelve recombinant plasmids. This recombinant plasmid, designated pEG212 consisting of pBR322 plus a 2.6 kb HindIII insert from strain EG2158, was selected for further experimentation and evaluation. The original *E. coli* colony harboring pEG212 was designated EG1313.

5.8 Location of the cryC Gene on the Cloned 2.6 KB HindIII Fragment.

It was likely that the cloned 2.6 kb HindIII fragment contained at least the NH2-terminal coding region of the cryC gene. Presence of the cryC gene on this fragment was verified using DNA sequencing to search for a region in the cloned 2.6 kb fragment that encoded the NH2-terminus of the coleopteran toxin. Since it is time-consuming to sequence a fragment of DNA longer than two kb it was necessary to identify a smaller fragment of DNA within the 2.6 kb fragment that would be expected to contain the $NH_2$-terminal coding region of the cryC gene. Accordingly plasmid pEG212 was digested with various restriction enzymes, digested plasmid was electrophoresed through an agarose gel and plasmid restriction fragments were blotted from the gel to a nitrocellulose filter. Hybridization of the filter with the radioactively labeled oligonucleotide probe revealed that the probe specifically hybridized to a 1.0 kb Pst 1 — EcoRI restriction fragment of DNA from pEG212. Therefore it was expected that the 1.0 kb Pstl - EcoRI fragment would contain at least the NH2-terminal coding region of the cryC gene.

The 1.0 kb fragment was subcloned from pEG212 into the DNA sequencing vectors mp18 and mp19 (Bethesda Research Laboratories, Bethesda MD). DNA sequencing of the 1.0 kb fragment revealed that it contained a region of DNA that encoded the NH2-terminal amino acids, with a few amino acid exceptions noted below, of the 70 kDa coleopteran toxin. This conclusively demonstrated that the cloned 2.6 kb HindIII fragment from the donor strain EG2158 contained the cryC gene.

5.9 DNA Sequence of the Cloned cryC Gene

A restriction map of the cloned 2.6 k fragment contained in plasmid pEG212 is shown in FIG. 7. The large arrow indicates a region of approximately 2.0 kb that was assumed to encode the entire coleopteran toxin. In order to determine the complete sequence of the cryC gene the entire 2.6 kb HindIII fragment in plasmid pEG212 was subcloned into the sequencing vectors mp18 and mp19. FIG. 8 shows the DNA sequence of the 2.6 kb HindIII fragment beginning with the first nucleotide in the HindIII site that is upstream from the cryC gene as shown on plasmid pEG212, FIG. 7. At nucleotide 569 (FIG. 8) a long open reading frame (protein coding region) was found beginning with an NH2-terminal methionine codon. Preceding the methionine codon is a ribosome binding site (GGAGGA) at nucleotide 557. At nucleotide 728, fifty-three amino acids downstream from the NH2-terminal methionine codon, the coding region for the NH2-terminus of the 71 kDa coleopteran toxin begins. This region encodes several aspartate and threonine residues that were determined by sequential Edman degradation of the 71 kDa protein to be threonine and aspartate residues, respectively (compare the NH2-terminal sequence of the 71 kDa protein with the coding region of the cryC gene beginning at nucleotide 728). These discrepancies are due to the difficulty in accurately determining the NH2-terminal amino acid sequence of proteins. Because of the precision with which DNA sequences can be determined the correct amino acid sequence for the coleopteran toxin must be as shown in FIG. 8.

As indicated in FIG. 8 the NH2-terminal coding region for the 71 kDa protein begins 53 amino acid residues downstream from the NH2-terminal methionine codon. Fifty-three amino acids are equivalent to approximately 6 kDa, precisely the difference in size between the 71 kDa protein and its assumed precursor of 77 kDa. Therefore, DNA sequencing of the cloned cryC gene clearly shows that the gene encodes a protein (77 kDa) that is subsequently proteolytically processed to yield a protein (71 kDa) that is 6 kDa smaller.

5.10 Use of the Cloned cryC Gene as a Specific Hybridization Probe.

5.10.1 Identification of Native B.t. Plasmids Containing cryC Genes.

One advantage of a cloned DNA sequence is that it can be used to identify related DNA sequences in uncharacterized samples of DNA. In the case of the cryC gene it is now possible that the cloned gene can be used to detect the presence of a cryC gene in a strain of B.t.

In order to determine whether the cloned cryC gene could be used to detect the presence and locations of a cryC gene in a native B.t. host strain the following procedure was carried out. B.t. strains HD1-1, and EG2158 were lysed according to the procedure of Eckhardt (Eckhardt, T. (1978) Plasmid 1:584-588) and the lysates were electrophoresed through agarose gels. This procedure allowed the separation by size of all plasmids contained in a particular strain. The separated plasmids were transferred from the agarose gel to a nitrocellulose filter by the blot procedure of Southern. The nitrocellulose filter was hybridized with the radioactively labeled 2.6kb HindIII (cryC gene) fragment. Autoradiography of the nitrocellulose filter revealed that the cryC gene fragment hybridized exclusively to one plasmid of approximately 88 MDa in the coleopteran toxin-producing strain EG2158 (FIG. 9). The cloned cryC gene did not hybridize to any plasmids in the coleopteran toxin-negative strain HD1-1. Therefore, this experiment demonstrated that the cloned cryC gene can be used in a direct manner to identify native plasmids containing cryC genes in B.t. strains. DNA hybridization with the cloned cryC gene allowed direct identification of a single plasmid carrying a cryC gene out of many such plasmids existing in strains of B.t.

5.11 Transformation of the cryC Gene Into Heterologous Microorganisms

The cryC gene can be inserted in any appropriate plasmid which may then be utilized to transform an appropriate microorganism. It is clearly within the scope of this invention that microorganisms other than B.t. may be transformed by incorporation of the cryC gene i.e., generally stated, organisms from the genera Bacillus and Escherichia. Preferred for use with this invention is the organism Bacillus megaterium.

The microorganisms so transformed will preferably produce the Coleoptera active protein toxin in quantities that are far in excess of the quantity of this toxin produced in a B.t. natural host strain. The coleopteran active toxin produced by a transformed organism is preferably the only delta-endotoxin produced by that organism. In this manner, the organism itself may be utilized alone or as part of an insecticidal composition. Since coleopteran active toxic would preferably be the only delta-endotoxin produced by the organism, it is a straightforward process to purify the coleopteran active protein from other cellular material by methods known in the art such as Renografin density gradients.

5.12 Transformation of the crtC Gene Into Plants

It is also within the scope of this invention that the cryC gene (FIG. 8) be inserted directly into a plant so that the plant itself produces the cryC coleopteran active toxin.

Genetic engineering of plants may be accomplished by introducing the desired DNA containing the cryC gene into plant tissues or cells using DNA molecules of a variety of forms and origins. These include, but are not limited to: DNA molecules derived from naturally occurring plant vectors such as the Ti plasmid from Agrobacterium tumefaciens or plant pathogens such as DNA viruses like Cauliflower Mosaic virus (CaMV) or Geminiviruses, RNA viruses, and viroids; DNA molecules derived from unstable plant genome components like extrachromosomal DNA elements in organelles (e.g., chloroplasts or mitochondria), or nuclearly encoded controlling elements; DNA molecules from stable plant genome components (e.g., origins of replication and other DNA sequences which allow introduced DNA to integrate into the organellar or nuclear genomes and to replicate normally, to autonomously replicate, to segregate normally during cell division and sexual reproduction of the plant and to be inherited in succeeding generations of plants).

DNA containing the cryC gene may be delivered into the plant cells or tissues directly by infectious plasmids, such as the Ti plasmid, viruses or microorganisms like A. tumefaciens, the use of liposomes, microinjection by mechanical methods and by whole chromosomes or chromosome fragments.

5.13 Products and Formulations Incorporating the Coleopteran Active Toxin

The coleopteran delta-endotoxin coded for by the cryC gene is a potent insecticidal compound with activity against coleopteran insects. It is, therefore, within the scope of the invention that this protein toxin be utilized as an insecticide (the active ingredient) alone, preferably in homogenous or pure form and having the amino acid sequence of FIG. 8, or as included within or in association with the B.t. strain EG2158 or with a transformed microorganism which expresses a cloned cryC gene or in a mixture of B.t. transconjugants or other transformed sporulating microorganisms containing cryC gene protein product toxin with spores or otherwise.

The compositions of the invention containing at least the cryC protein toxin are applied to the appropriate Coleoptera (or Lepidoptera) habitat at an insecticidally effective amount which will vary depending on such factors as, for example, the specific coleopteran (or also lepidopteran if a dual active transconjugant is used) insects to be controlled, the specific plant to be treated and the method of applying the insecticidally active compositions.

Target crops (potential habitats for Coleoptera and Lepidoptera) protected by the present invention comprise e.g. the following species of plants: cereals (such as wheat, barley, rye, oats, rice, sorghum and related crops), beets, leguminous plants, oil plants (such as poppy, olives, and sunflowers) cucumber plants, fiber plants, citrus fruit, vegetables, deciduous trees and conifers.

The preferred insecticide formulations are made by mixing EG2158 alone or any mutant, recombinant or genetically engineered derivative thereof, in an effective amount or the coleopteran active toxin alone or incorporated in or associated with another organism (i.e. a transformed organism or transconjugant), with the desired carrier. The formulations may be administered as a dust or as a suspension in oil (vegetable or mineral) or water, a wettable powder or in any other material suitable for agricultural application, using the appropriate carrier adjuvants. Suitable carriers can be solid or liquid and correspond to the substances ordinarily employed in formulation technology, e.g., natural or regenerated mineral substances, solvents, dispersants, wetting agents, tackifiers, binders or fertilizers.

Generally stated, the preferred compositions usually contain 0.1 to 99%, preferably 1 to 50%, of the insecticidal microorganism such as Bacillus thuringiensis, or combination thereof with other active ingredients, 1 to 99.9% of a solid or liquid adjuvant, and 0 to 25% preferably 0.1 to 20%, of a surfactant.

The formulations containing a solid or liquid adjuvant, are prepared in known manner, e.g., by homogenously mixing and/or grinding the active ingredients with extenders, e.g., solvents, solid carriers, and in some cases surface active compounds (surfactants).

Suitable liquid carriers are vegetable oils, such as coconut oil or soybean oil, mineral oils or water. The solid carriers used, e.g., for dusts and dispersible powders, are normally natural mineral fibers such as calcite, talcum, kaolin, or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite. Suitable nonsorbent carriers are materials such as silicate or sand. In addition, a great number of pregranulated materials or inorganic or organic mixtures can be used, e.g., especially dolomite or pulverized plant residues.

Depending on the nature of the active ingredients to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface active compounds.

Suitable soaps are the alkali metal salts, alkaline earth metal salts or unsubstituted ammonium salts of higher fatty acids ), ($C_{10}$-$C_{11}$), e.g., the sodium or potassium salts of oleic or stearic acid, or natural fatty acid mixtures which can be obtained, e.g., from coconut oil or tallow oil. Further stable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the forms of alkali metal salts, alkaline earth metal salts or unsubstituted ammonium salts and generally contain a $C_6$-$C_{22}$ alkyl, e.g., the sodium or calcium salt of dodecylsulfate, or of a mixture of fatty alcohol sulfates, obtained from fatty acids. These compounds also comprise the salts of sulfonic acid esters and sulfonic acids of fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g., salts of the phosphoric acid ester of an adduct of p-nonylphenol with 4 to 14 moles of ethylene oxide.

Nonionic surfactants are preferably a polyglycol ether derivative or aliphatic or cycloaliphatic alcohol or saturated or unsaturated fatty acids and alkylphenols, said derivative containing 3 to 10 glycol ether groups and 8 to 20 carbon atoms in the (aliphatic) hydrocarbon moiety and 6 to 18 carbon atoms in the alkyl moiety of the alkylphenols.

Other suitable non-ionic surfactants are the water soluble adducts of polyethylene oxide with alkylpropylene glycol, ethylenediaminopolypropylene glycol and alkylpolypropylene glycol contain 1 to 10 carbon atoms in the alkyl chain, which adducts contain 20 to 250 ethylene glycol ether groups and 10 to 100 propylene glycol ether groups.

Representative examples of non-ionic surfactants are nonylphenolpolyethoxyethanols, castor oil, glycol ethers, polypropylene/polyethylene oxide adducts, tributylphenoxypolyethoxyethanol, ethylene glycol and octylphenoxypolyethoxynethanol. Fatty acid esters of polyoxyethylene sorbitan, such as polyoxyethylene sorbitan trioleate, are also suitable non-ionic surfactants.

Cationic surfactants are preferably quaternary ammonium salts which contain, as substituents on the nitrogen, at least one $C_8$-$C_{22}$ alkyl radical and, as further substituents, lower unsubstituted or halogenated alkyl benzyl, or hydroxylated lower alkyl radicals. The salts are preferably in the form of halides, methyl sulfates or ethylsulfates, e.g., stearyltrimethylammonium chloride.

6.0 EXAMPLES

The insecticidal activity of B.t., transformed or non-transformed *Bacillus megaterium* and of transformed *Escherichia coli* was determined by including various amounts of these microorganisms in a test diet which was fed to insects. After feeding, insect mortality was measured.

Specifically, these bioassays involved growing the microorganism to stationary phase in liquid culture or on solid agar base media for two days at 30° C. For *E. coli* harboring plasmids the media was LB containing 40 ug/ml ampicillin. For *B. megaterium* harboring plasmids the media was DS containing 10 ug/ml tetracycline. The microorganisms were harvested from the solid medium by scraping with a spatula. The wet weight of the harvested bacteria was determined and bacterial cells were resuspended to a known concentration in deionized water. 100 ul of the bacterial cell suspension was topically applied to 3 ml of a solid agar-based artificial diet in a feeding cup. The top surface area of the diet was 600 square millimeters. One neonate larva of Colorado potato beetle (CPB) was placed in each feed cup and mortality was scored after seven days.

6.1 Example 1

Transformation of the cryC Gene into Bacillus Megaterium

The purpose of this example was to determine whether the cloned cryC gene would be expressed in *Bacillus* strains. Plasmid pEG212 (containing the cryC gene) will replicate only in gram-negative strains such as *E. coli*. In order to test for the expression of the cloned cryC gene in a *Bacillus* strain it was first necessary to construct a recombinant plasmid that contained the cryC gene and that was capable of replicating in Bacillus. A *Bacillus-E. coli* "shuttle vector" that contained the cryC gene was constructed. The term "shuttle vector" indicates that the plasmid is capable of replication both in *Bacillus* and in *E. coli*. The *E. coli-Bacillus* shuttle vector was constructed by digestion of the *Bacillus* plasmid pBC16 (tetracycline resistance) with SphI, ligation of the digested plasmid into the SphI site of pEG212 (ampicillin resistance) and transformation of *E. coli* to ampicillin and tetracycline resistance.

One tet and amp resistant *E. coli* transformant harbored a plasmid (designated pEG213) that was composed of pBC16 inserted into the SphI site of pEG212 (FIG. 7). FIG. 7 shows the restriction map of plasmid pEG213. The areas denote plasmid vector DNA. The open box is pBR322 DNA (*E. coli* replication) and the cross-hatched box is pBC16 DNA (*Bacillus* replication). The horizontal line is cloned DNA from strain EG2158. The large arrow denotes the coding region of the cryC gene. pEG213 was transformed into *Bacillus megaterium* (ATCC deposit number 35985) and one tetracycline resistant transformant harboring pEG213 (designated strain EG1314) was chosen for further study.

This example determined if the cloned cryC gene was expressed in the recombinant *B. megaterium* strain EG1314 (pEG213). Gene expression was measured by the technique of NadodeSO4/polyacrylamide gel electrophoresis. Generally, the technique involved preparation of cell lysates, electrophoresis of cell lysates through a NadodeS04/polyacrylamide gel and staining of the gel to permit visualization of proteins.

Specifically, the technique was carried out as follows: *B. megaterium* cells were grown on DS plates containing 10ug/ml tetracycline for 48 hr. at 30° C. *B. thuringiensis* strain EG2158 was grown similarly to *B. megaterium* except the DS plates contained no tetracycline. After this period almost all cells had entered the stationary phase of growth. Cells were harvested with a spatula and resuspended in deionized water. A portion of the cell suspension was mixed 1:2 vol:vol with preheated (70° C.) gel loading buffer (5% Beta-mercaptoethanol, 2% NaDodeS04, 60 mM Tris pH 6.8, 10% glycerol) and incubated at 70° C. for 7 min. The suspension was centrifuged briefly, after centrifugation the supernatant was immediately loaded onto an NadodeSO4/-polyacrylamide gel and the proteins in the supernatant were resolved by gel electrophoresis according to the method of Laemmli. (1973) J. of Mol. Bio., 80:575-599) The proteins in the gel were visualized by staining the gel with Coomassie dye.

FIG. 10 is a photograph of an NadodeSO4/polyacrylamide gel that had been prepared as described above. The lane labeled STND in FIG. 10 contained protein molecular weight standards. Numbers to the right of the gel indicate protein sizes in kilodaltons (kDa). The lane labeled EG2158 contained extracts of that B.t. strain. The major protein band that corresponded to the coleopteran toxin protein is indicated by an arrow. The lane labeled CRY contained a portion of the purified coleopteran toxin protein. The coleopteran toxin protein was purified as described above.

The lanes labeled EG1311 and EG1314 in FIG. 10 contained extracts of these *B. megaterium* strains harboring pBC16 and pEG213(cryC) respectively. A comparison of lanes EG1311 and EG1314 showed that extracts of strain EG1314(pEG213) contained a major protein that corresponded in size to that of the coleopteran toxin protein. This protein was not present in extracts of strain EG1311(pBC16). This demonstrates that *B. megaterium* harboring the cloned cryC gene synthesized high levels of the coleopteran toxin protein. In addition, when viewed under the light microscope the cells of strain EG1314 appeared to contain phase-bright protein inclusion bodies characteristic of crystal toxins.

6.2 Bioassay of the Expression Product of the Cloned cryC Gene in *B. Megaterium*

*B. megaterium* strain EG1314 (pEG213-cryC) was tested for toxicity against Colorado potato beetle (CPB). A cell suspension was prepared by growing strains EG1311 (pBC16-negative control) and EG1314 on solid DS medium containing 10 ug/ml tetracycline for 48 hours at 30° C. Cells were harvested with a spatula and cells were resuspended in deionized water. The bacterial cell suspensions were topically applied to 3 ml of a solid agar-base artificial diet in a feeding cup. One neonate larva of CPB was added per cup and mortality was scored after seven days. (TABLE VI)

TABLE VI

| Dose-mg cells/ml | CPB larvae # dead/total |
|---|---|
| EG1311 (pBC16-control) - 0.2 mg/cup | 3/50 |
| EG1314 (pEG213-cryC) - 0.2 mg/cup | 49/50 |

7 0 DEPOSIT OF MICROORGANISMS

It is within the scope of this invention that a wide variety of both sporulating and nonsporulating microorganisms may be transformed with the cryC gene as described herein. Exemplary of the microorganisms which may be engineered are those from the genera *Bacillus* and *Escherichia*. Preferred for use with this invention is the organism *Bacillus megaterium*. In addition, the following *Bacillus thuringiensis, Bacillus megaterium* and *E. coli* strains which are also preferred for use with this invention and which carry the listed plasmids have been deposited with the Agricultural Research Culture Collection (NRRL), Peoria, Ill. and have been assigned the listed accession numbers:

| strain | Plasmids | Accession Numbers |
|---|---|---|
| B. thuringiensis | | |
| EG2158 | Several naturally occurring, including the 88-Md coleopteran toxin plasmid | B-18213 |
| EG2421 (HD263-8-5) | Several naturally occurring plasmids, including a 60-Md lepidopteran toxin plasmid, as well as the 88-Md toxin plasmid from EG2158 | B-18212 |
| EG2424 (HD263-8-73) | Several naturally occurring plasmids, including a 60-Md lepidopteran toxin plasmid, plus the 88-Md toxin plasmid from EG2158 and a 44-Md lepidopteran toxin plasmid from HD-279. | B-18214 |
| B. megaterium EG1314 | pEG213 | B-18210 |
| E. coli EG1313 | pEG212 | B-18211 |

The present invention is not to be limited in scope by the microorganisms deposited, since the deposited embodiments are each intended as a single illustration of one aspect of the invention. Indeed, various modifications of the invention in addition to those shown and described herein will become apparent to those skilled in the art from the foregoing description and accompanying drawings.

What is claimed is:

1. A *Bacillus thuringiensis* bacterium that produces protein endotoxins having insecticidal activity against lepidopteran and coleopteran insects, the coleopteran-active endotoxin being produced by an acquired coleopteran toxin-encoding plasmid that is characteristic of *Bacillus thuringiensis* strain EG2158, deposited with the NRRL and assigned NRRL Accession No. B-18213.

2. The *Bacillus thuringiensis* bacterium of claim 1 wherein the plasmid is about 88 MDa in size.

3. An insecticide for controlling coleopteran and lepidopteran insects comprising a mixture of *Bacillus thuringiensis* bacteria of claim 1 and an argiculturally-acceptable carrier.

4. The *Bacillus thuringiensis* bacterium of claim 1 wherein the bacterium which produces protein endotoxins having insecticidal activity against lepidopteran and coleopteran insects is a *Bacillus thuringiensis* subspecies *kurstaki*.

5. A *Bacillus thuringiensis* bacterium, deposited with the NRRL and assigned NRRL Accession No. B-18212, that produces protein endotoxins having insecticidal activity against lepidopteran and coleopteran insects, the coleopteran-active endotoxin being produced by an acquired coleopteran toxin-encoding plasmid.

6. An insecticide for controlling coleopteran and lepidopteran insects comprising a mixture of *Bacillus thuringiensis* bacteria of claim 5 and an agriculturally-acceptable carrier.

7. A *Bacillus thuringiensis* bacterium, deposited with the NRRL and assigned NRRL Accession No. B-18214, that produces protein endotoxins having insecticidal activity against lepidopteran and coleopteran insects, the coleopteran-active endotoxin being produced by an acquired coleopteran toxin-encoding plasmid.

8. An insecticide for controlling coleopteran and lepidopteran insects comprising a mixture of *Bacillus thuringiensis* bacteria of claim 7 and an agriculturally-acceptable carrier.

9. A method for producing a *Bacillus thuringiensis* bacterium having insecticidal activity against lepidopteran and coleopteran insects comprising providing a *Bacillus thuringiensis* recipient strain, characterized by containing at least one lepidopteran toxin encoding plasmid but having no coleopteran-active toxin encoding plasmids;

providing *Bacillus thuringiensis* strain EG2158 deposited with the NRRL and assigned NRRL Accession No. B-18213 as the donor strain carrying a coleopteran toxin encoding plasmid that is capable of being acquired by the recipient strain;

introducing the two *Bacillus thuringiensis* strians into close proximity under conditions inducing plasmid conjugal transfer to effect transfer of the coleopteran toxin encoding plasmid into the recipient strain; and isolating and recovering a transconjugant *Bacillus thuringiensis* strain that produces protein endotoxins having insecticidal activity against lepidopteran and coleopteran insects.

10. The method of claim 9 which further comprises providing a second *Bacillus thuringiensis* donor strain carrying a transferable lepidopteran toxin encoding plasmid; introducing the second *Bacillus thuringiensis* donor strain into close proximity with the transconjugant *Bacillus thuringiensis* strain under conditions inducing plasmid conjugal transfer, to effect transfer of the lepidopteran toxin encoding plasmid from the second donor strain into the transconjugant strain; and recovering a transconjugant *Bacillus thuringiensis* strain that contains multiple lepidopteran toxin encoding plasmids and produces protein endotoxins having insecticidal activity against lepidopteran and coleopteran insects.

11. A *Bacillus thuringiensis* bacterium deposited with NRRL and assigned Accession No. B-18213.

12. An insecticide for controlling coleopteran insects comprising a mixture of *Bacillus thuringiensis* bacteria of claim 11 and an agriculturally-acceptable carrier.

* * * * *